(12) United States Patent
Lambrechts

(10) Patent No.: US 10,294,529 B2
(45) Date of Patent: May 21, 2019

(54) MICROSATELLITE INSTABILITY MARKERS IN DETECTION OF CANCER

(71) Applicants: VIB VZW, Ghent (BE); Life Sciences Research Partners VZW, Leuven (BE)

(72) Inventor: Diether Lambrechts, Kessel-Lo (BE)

(73) Assignees: Life Sciences Research Partners VZW, Leuven (BE); VIB VZW, Ghent (BE)

( * ) Notice: Subject to any disclaimer, the term of this patent is extended or adjusted under 35 U.S.C. 154(b) by 420 days.

(21) Appl. No.: 13/860,422

(22) Filed: Apr. 10, 2013

(65) Prior Publication Data

US 2013/0267426 A1 Oct. 10, 2013

Related U.S. Application Data

(60) Provisional application No. 61/638,955, filed on Apr. 26, 2012, provisional application No. 61/622,383, filed on Apr. 10, 2012.

(51) Int. Cl.
*C12Q 1/6886* (2018.01)

(52) U.S. Cl.
CPC ..... *C12Q 1/6886* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 4,851,331 A | 7/1989 | Vary et al. | |
| 5,137,806 A | 8/1992 | Lemaistre et al. | |
| 5,210,015 A | 5/1993 | Gelfand et al. | |
| 5,310,893 A | 5/1994 | Erlich et al. | |
| 5,451,512 A | 9/1995 | Apple et al. | |
| 5,468,613 A | 11/1995 | Erlich et al. | |
| 5,487,972 A | 1/1996 | Gelfand et al. | |
| 5,491,063 A | 2/1996 | Fisher et al. | |
| 5,571,673 A | 11/1996 | Picone et al. | |
| 5,595,890 A | 1/1997 | Newton et al. | |
| 5,604,099 A | 2/1997 | Erlich et al. | |
| 5,639,611 A | 6/1997 | Wallace et al. | |
| 5,804,375 A | 9/1998 | Gelfand et al. | |
| 5,994,056 A | 11/1999 | Higuchi et al. | |
| 6,664,064 B1 | 12/2003 | Dietmaier | |
| 2001/0053519 A1* | 12/2001 | Fodor et al. | B01J 19/0046 435/6.11 |
| 2015/0045369 A1 | 2/2015 | Lambrechts | |

FOREIGN PATENT DOCUMENTS

| | | |
|---|---|---|
| CN | 102230004 | 11/2011 |
| EP | 235726 A2 | 5/1993 |
| EP | 487218 A1 | 12/1997 |
| EP | 512334 A2 | 9/1999 |
| WO | 8911548 | 11/1989 |
| WO | 9322456 A1 | 11/1993 |
| WO | 2012166151 A1 | 12/2012 |
| WO | 2013153130 A1 | 10/2013 |

OTHER PUBLICATIONS

Subramanian et al., "Genome-wide analysis of microsatellite repeats in humans: their abundance and density in specific genomic regions," Genome Biology 2003, 4:R13.*
Bentley et al., "Accurate whole human genome sequencing using reversible terminator chemistry," Nature 2008, 456:53-59.*
Umar et al., Revised Bethesda Guidelines for Hereditary Nonpolyposis Colorectal Cancer (Lunch Syndrome) and Microsatellite Instability, JNCI Journal of the National Cancer Institute, Feb. 18, 2004, pp. 261-268, vol. 96, No. 4.
Morandi et al., T-[20] repeat in the 3'-untranslated region of the MT1X gene: a marker with high sensitivity and specificity to detect microsatellite instability in colorectal cancer, International Journal of Colorectal Disease, Nov. 23, 2011, pp. 647-656, vol. 27, No. 5.
Mao et al., Evidence that a mutation in the MLH1 3'-untranslated region confers a mutator phenotype and mismatch repair deficiency in patients with relapsed leukemia, Journal of Biological Chemistry, Feb. 2008, pp. 3211-3216, vol. 283, No. 6.
Gaymes et al., Microsatellite Instability (MSI) in High Risk Myelodysplastic Syndrome (MDS) and Acute Myeloid Leukaemia (AML) Cells Promotes Frameshift Mutations in DNA Repair Genes: Indications for PARP Inhibitor Therapy, Blood, Nov. 1, 2010, pp. 513, vol. 116, No. 21.
Gu et al., Down-regulation of MLH1 in a relapsed leukemia patient is associated with a three-nucleotide deletion in the MLH1 3' untranslated region, FASEB Journal, Apr. 2008, vol. 22, No. 776, (2 pages).
Ruggiero et al., Deletion in a (T)8 microsatellite abrogates expression regulation by 3'-UTR, Nucleic Acids Research, Nov. 15, 2003, pp. 6561-6569, vol. 31, No. 22.
Yuan et al., An A13 Repeat within the 3'-Untranslated Region of Epidermal Growth Factor Receptor (EGFR) Is Frequently Mutated in Microsatellite Instability Colon Cancers and Is Associated with Increased EGFR Expression, Cancer Research, Oct. 2009, pp. 7811-7818, vol. 69, No. 19.
Ahmed et al., Molecular markers that predict response to colon cancer therapy, Expert Review of Molecular Diagnostics, May 1, 2005, pp. 353-375, vol. 5, No. 3.
PCT International Search Report, PCT/EP2013/057516, dated Jun. 6, 2013.
Suraweera et al., Conservation and mononucleotide repeats within 3' and 5' untranslated regions and their instability in MSI-H colorectal cancer, Oncogene, 2001, pp. 7472-7477, vol. 20.

(Continued)

*Primary Examiner* — Kaijiang Zhang
(74) *Attorney, Agent, or Firm* — Patent Law Works LLP

(57) ABSTRACT

The present application relates to the field of cancer, particularly to mismatch repair (MMR-) deficient tumors. New markers are presented herein that have a high sensitivity to detect whether a tumor is mismatch repair deficient or not. The markers are particularly mutations in microsatellite regions. Accordingly, methods are provided for diagnosing microsatellite instability of a tumor, comprising determining the presence of these markers. Further, kits are provided to detect the presence of these markers (or subsets thereof) in a sample.

24 Claims, 11 Drawing Sheets

(56) References Cited

OTHER PUBLICATIONS

Boland, et al. "A National Cancer Institute Workshop on Microsatellite Instability for Cancer Detection and Familial Predisposition: Development of International Criteria for the Determination of Microsatellite Instability in Colorectal Cancer." Cancer Research. 58.22 (1998): 5248-5257. PubMed PMID: 9823339.

Serrano, et al. "Bethesda Criteria for Microsatellite Instability Testing: Impact on the Detection of New Cases of Lynch Syndrome." Familial Cancer. 11.4 (Dec. 2012): 571-578. doi: 10.1007/s10689-012-9550-6. PubMed PMID: 22776989.

Suraweera N, Duval A, Reperant M, Vaury C, Furlan D, Leroy K, Seruca R, Iacopetta B, Hamelin R. Evaluation of tumor microsatellite instability using five quasimonomorphic mononucleotide repeats and pentaplex PCR. Gastroenterology. Dec. 2002;123(6):1804-11. PubMed PMID: 12454837.

Vilar E, Bartnik CM, Stenzel SL, Raskin L, Ahn J, Moreno V, Mukherjee B, Iniesta MD, Morgan MA, Rennert G, Gruber SB. MRE11 deficiency increases sensitivity to poly(ADP-ribose) polymerase inhibition in microsatellite unstable colorectal cancers. Cancer Research. Apr. 1, 2011;71(7):2632-42. doi: 10.1158/0008-5472.CAN-10-1120. Epub Feb. 7, 2011. PubMed PMID: 21300766; PubMed Central PMCID: PMC3407272.

Wilding JL, McGowan S, Liu Y, Bodmer WF. Replication error deficient and proficient colorectal cancer gene expression differences caused by 3UTR polyT sequence deletions. Proc Natl Acad Sci U S A. Dec. 7, 2010;107(49):21058-63. doi:10.1073/pnas.1015604107. Epub Nov. 19, 2010. PubMed PMID: 21097699; PubMed Central PMCID: PMC3000307.

\* cited by examiner

MICROSATELLITE INSTABILITY MARKERS IN DETECTION OF CANCER

CROSS-REFERENCE TO RELATED APPLICATION(S)

This application claims the benefit under 35 U.S.C. § 119(e) of U.S. Ser. No. 61/622,383, filed on Apr. 10, 2012 and U.S. Ser. No. 61/638,955, filed on Apr. 26, 2012.

FIELD OF THE INVENTION

The present application relates to the field of cancer, particularly to mismatch repair (MMR−) deficient tumors. New markers are presented herein that have a high sensitivity to detect whether a tumor is mismatch repair deficient or not. The markers are particularly mutations in microsatellite regions. Accordingly, methods are provided for diagnosing microsatellite instability of a tumor, comprising determining the presence of these markers. Further, kits are provided to detect the presence of these markers (or subsets thereof) in a sample.

BACKGROUND

The form of genomic instability associated with defective DNA mismatch repair in tumors is called microsatellite instability (MSI). Microsatellite instability (MSI) is a clonal change in the number of repeated DNA nucleotide units in microsatellites. It typically arises in tumors with defective mismatch repair (MMR) genes: failure of the DNA MMR system to repair errors that occur during the replication of DNA results in accelerated accumulation of single nucleotide mutations and alterations in the length of simple, repetitive microsatellite sequences that occur ubiquitously throughout the genome. MMR-deficiency represents a well-established cause of Lynch syndrome, which is an autosomal dominant inherited disorder of cancer susceptibility that affects 2% tot 5% of endometrial or colorectal cancers. Lynch syndrome is caused by mutations or deletions in the MMR pathway genes (MLH1, MSH2, MSH3, MSH6 or PMS2). Additionally, epigenetic silencing of the MLH1 promoter is responsible for up to 20% of 'sporadic' colorectal cancers. Additionally, MMR-deficiency has also been described in a minority of ovarian, pancreatic, gastric, leukemic, as well as several other cancers. Profiling of mutation spectra in cells engineered to have an MMR-deficient (MMR−) system has been widely used to characterize genetic 'errors' occurring during DNA replication. Although studies characterizing these mutation spectra have been limited to observations at one or a few reporter loci, or have focused exclusively on mutations at known hotspot sequences, they have helped to understand the mechanisms of the intrinsic DNA repair process. It was found, for instance, that mismatch mutations mostly occur in repetitive DNA sequences, whereby MSH6 is involved in the recognition of insertion-deletions of 1 or 2 bases and MSH3 is responsible for longer insertion-deletion loops.

MMR− tumors are characterized by a distinct response to standard chemotherapies, such as 5-fluoracil and the alkylating agents such as temozolomide. Alternative approaches focusing on the aberrant DNA repair processes of MMR− tumors have therefore been proposed. Synthetic lethality approaches have shown, for instance, that increased oxidative damage (by methotrexate exposure or PINK1 silencing) or interference with the base excision repair (BER) pathway (by DNA polymerase γ or β inhibition) sensitizes MMR− tumors. In particular, in MMR− tumors, oxidative damage induces 8-oxoguanine (8-oxoG) DNA lesions, which fail to be sufficiently repaired either by the BER or MMR pathway, generating mainly GC to TA dinucleotide transversions at the DNA level, leading to cell death. Additionally, it has been hypothesized that there is a maximum mutation frequency that a tumor can tolerate, above which a further increase in mutations would be detrimental. It has therefore been proposed to additionally treat MMR− tumors with mutagenic nucleoside analogues until a critical level of mutations is obtained resulting in error catastrophe-like ablation of the tumor. MMR− tumors are often also resistant to targeted cancer therapies, including anti-EGFR and anti-VEGF therapies. Although the precise reasons for this resistance are unknown, presence of secondary mutations in established tumor driver genes as a consequence of MMR− might be responsible. For instance, MMR− tumors can acquire mutations in double-strand break repair genes (e.g., MRE11, ATR and RAD50), known oncogenes or tumor suppressors (e.g., PIK3CA or PTEN). Since presence of MMR-deficiency mainly in colorectal and endometrial tumors represent a familial form of cancer, and since tumors exhibiting mutation spectra characteristic of MMR-deficiency, diagnostic tests assessing MMR-deficiency are commonly used. By far the most common method to detect MSI is to measure the length of a polymerase chain reaction amplicon containing the entire microsatellite. This requires DNA, a pair of primers of which one is often fluorescently end labeled, a sequencer, and suitable software. Alternatively, if the amplicon is sequenced, one can simply count the number of repeat units. MSI can also be indirectly diagnosed by detecting loss of staining by immunohistochemistry (IHC) of one of the mismatch repair genes, since this also points to an abnormality in mismatch repair. Immunohistochemical and genetic methods are both characterized by a considerable number of false-negatives, and for this reason combined assessments at the immunohistochemical and genetic level are performed in a routine diagnostic setting.

There are at least 500 000 microsatellites in the human genome, and because defective MMR does not affect all microsatellites in a given tumor, it is important to study more than one microsatellite and to study microsatellites that are frequently affected by instability. As microsatellite markers were originally quite randomly picked by researchers, based on their own experiments, a conference was held in Bethesda, Md., to discuss the issues and make suggestions to promote consistency across studies. This resulted in a recommendation for a "golden standard" marker panel, known as the Bethesda panel[9]. This panel consists of three dinucleotide repeats (D2S123, D5S346, D17S250) and two mononucleotide repeats (BAT26, BAT25) and is still the standard test for MSI. It was proposed to consider a tumor MSI-positive if 40% or more of the markers tested were unstable (also referred to as MSI-high or MSI-H). When using the five-marker panel, this means that MSI is called when at least two of them are positive; however, often four or all five are positive in tumors with MSI. Tumors that test negative for all five markers are termed microsatellite stable (MSS). For tumors that tested positive on 1 tumor marker (or on <30% of tumor markers), the term MSI-L was proposed[9].

Although the Bethesda panel is still considered the standard, it is known to have a fairly low sensitivity (also depending on which MMR gene is mutated). For instance, for patients with MLH1 mutations, sensitivity is 80%, but for patients with MSH6 mutations, it is only 55%[10]. This can be improved by adding further markers[10], but still actual MSI-H patients may present as MSI-L or MSS. This is not without significance, as MSI status is important in prognosis (typically better for MSI-H patients[11]), treatment (MSI-H tumors do not respond to fluoro-uracil(FU)-based adjuvant therapy, as an intact MMR system is needed to induce apoptosis of cells with FU-modified DNA[11-13]), and diagnosis of several cancers (e.g. those of the Lynch syndrome), and newly diagnosed colorectal cancer (CRC) patients are routinely screened for MSI status.

Another significant disadvantage is that the Bethesda panel is only recommended for colon cancer, even though other cancers displaying MSI are known[9]. It seems that this is due to the fact that the five markers were rather randomly identified as being mutated in microsatellite unstable colon cancer, but there is no biological mechanism known.

A further disadvantage is of a technical nature. The Bethesda marker panel contains quite long repeats (e.g. the BAT26 marker contains a 26 nucleotide A repeat), and the typical PCR products used to determine MSI status are well over 100 bp. To accurately sequence these fragments and determine the exact length of the repeat, Sanger based sequencing methods in conjunction with multicapillary gel electrophoresis are typically used. However, more and more labs use so called "next generation" sequencing which employ massively parallel sequencing techniques. While cheaper, these technologies make use of shorter reads and cannot be used to detect microsatellite instability on the Bethesda marker panel. As a consequence, labs need to maintain two sequencers: one for Bethesda marker panel screening, and one for other experiments. It would be far more convenient if no special sequencer was required for determining MSI status and this determination could be done on commonly used equipment.

Thus, it would be advantageous to find markers for microsatellite instability that are more sensitive than the currently used Bethesda panel, while retaining specificity for MSI. Ideally, these markers are found using unbiased detection methods (i.e., looking across the whole genome rather than checking specific regions that are supposed to be altered in disease setting). A further advantage would be the identification of markers that are indicative of MSI as such. That is to say, they are a general marker for microsatellite instability, and not just for microsatellite instability in colon cancer (as is the case for the Bethesda panel). This would indeed obviate the need to find new markers for each cancer where MSI can be present. An additional advantage would be the identification of markers whose status can be determined independently of technology. More particularly, markers that can be identified using next generation sequencing technologies (instead of only being identified using Sanger sequencing). This way, labs need not to hold on to an apparatus they only use for checking the Bethesda panel markers.

SUMMARY

It is an object of the invention to provide better markers for determining MSI status of a particular cancer. To make sure detection was unbiased, we here report, for the first time, next-generation sequencing of mismatch-repair deficient tumors. The markers are chosen not to be in long microsatellites such that their detection is not dependent on Sanger sequencing methodology. Further, to expand applicability of markers, markers were evaluated in different tumor types such that they represent markers of microsatellite instability across various cancers, and not cancer type-specific markers. Finally, markers were selected to occur recurrently in the tumors.

As will be expanded upon in the Examples section, next-generation sequencing allowed the identification of a new panel of markers that can be used to detect MMR-deficiency and that was in agreement with these conditions. Most particularly, these markers are indels present in microsatellite regions in coding and (most particularly) non-coding regions of specific genes.

Accordingly, methods are provided herein of diagnosing MSI status of a tumor, comprising determining the presence of an indel in at least two microsatellite regions in a sample of the tumor DNA, wherein the at least two microsatellite regions are at least two microsatellite regions present in 5' UTR or 3' UTR regions from the genes listed in Table 1, or at least three microsatellite regions selected from those present in the exons of the genes listed in Table 2 and/or present in 5' UTR or 3' UTR regions from the genes listed in Table 1, wherein the presence of at least one indel is indicative of MSI.

According to further particular embodiments, the microsatellite regions are homopolymer regions. According to yet further particular embodiments, the microsatellite regions are identical to the microsatellite regions identified in Table 1 or 2.

According to particular embodiments, the cancer or tumor for which the MSI status is diagnosed is selected from the group of: colorectal cancer, endometrial cancer, ovarian cancer, gastric cancer, leukemia, and a tumor of the Lynch syndrome.

As indels in microsatellites in non-coding regions (such as the 5' and 3' UTR regions) are subjected to less selection pressure than indels in coding regions (whereby the latter cause frameshift mutations resulting in a completely different translation from the original), it could be demonstrated that indels in microsatellites from non-coding regions are more reliable markers of MSI across cancer types. In fact, over 50% of the non-coding markers identified herein score positive when tested on MMR-deficient tumors with proven MSI. For the exonic markers, still well over ⅓ scored positive when tested on these tumors. This explains why it is envisaged to use at least three markers when at least part of the markers is in exonic regions.

It is also particularly envisaged to use combinations of markers in exonic regions and markers in non-coding regions. For instance, according to particular embodiments, the at least two microsatellite regions wherein the presence of an indel is determined are at least two microsatellite regions selected from those present in 5' UTR or 3' UTR regions from the genes listed in Table 1 and at least two microsatellite regions selected from those present in the exons of the genes listed in Table 2.

According to specific embodiments, it is envisaged to use more markers than at least two or three. Using more markers will typically yield a more accurate diagnosis (although this benefit should be off-set to the increased cost. Also, once above a certain threshold of markers, the relative value of adding another marker is limited, as it does not necessarily add information). Thus, according to particular embodiments, at least four, five, six, seven or eight markers are used (i.e. indels in microsatellite regions selected from those present in the exons of the genes listed in Table 2 and/or present in 5' UTR or 3' UTR regions from the genes listed in Table 1). According to further particular embodiments, the presence of at least 8, 9, 10, 11 or 12 indels in microsatellite regions selected from those present in the exons of the genes listed in Table 2 and/or present in 5' UTR or 3' UTR regions from the genes listed in Table 1 are used to determine the MSI status. According to even further particular embodiments, yet even more markers are used, e.g. at least 15, at least 20, at least 25, at least 30, at least 35, at least 40 markers, or at least 50 markers.

According to specific embodiments, at least one marker used is an exonic marker in a gene not previously associated with cancer, or in a gene not previously known to be affected in MMR deficient tumors. Thus, it is envisaged that the microsatellite(s) selected from those present in the exons of the genes listed in Table 2 comprises at least one microsatellite present in a gene selected from the list of: SETD1B, RBMXL1, CCDC150, TMEM60, DDX27, EXOSC9, FAM111B, KIAA0182, KIAA1919, OR7E24, P4HTM, PRRT2, RNPC3, and TMEM97. According to yet even more specific embodiments, at least one microsatellite is present in a gene selected from the list of: SETD1B, TMEM60, DDX27, EXOSC9, FAM111B, and KIAA1919. According to alternative embodiments, SEC31A can also be used in these lists.

A particularly envisaged marker panel are the microsatellites in the genes shown in Table 3. Thus, according to these embodiments, methods are provided wherein the presence of an indel in at least two microsatellite regions in a sample of the tumor DNA is determined, wherein the at least two microsatellite regions are microsatellite regions from the 58 genes shown in Table 3.

According to particular embodiments, MSI status can be further characterized as follows: if 20% or more of the studied microsatellite regions contains an indel, the tumor is MSI-H, if between 2.5% and 20% of the microsatellite regions contains an indel, the tumor is MSI-L, and if less than 2.5% of the microsatellite regions contains an indel, the tumor is microsatellite stable (MSS).

According to a specific aspect, the microsatellite indel markers provided herein can be detected independent of the technology used. However, it is particularly envisaged that determining the presence of an indel is not done through a method based on Sanger sequencing. This because the process of detecting microsatellite instability using the Bethesda marker panel is typically done through Sanger sequencing, a protocol that proves quite cumbersome. According to further embodiments, it is particularly envisaged to determine the presence of an indel through single basepair extension methods (such as a Sequenom MassArray), DNA hybridization technologies (e.g. Taqman) or a similar technology.

According to another aspect, a biomarker panel is provided for determining MSI in a tumor sample. Such biomarker panel comprises at least eight microsatellite regions selected from those present in 5' UTR or 3' UTR regions from the genes listed in Table 1 and those present in the exons of the genes listed in Table 2. According to very particular embodiments, the biomarker panel comprises at least half of the microsatellite regions listed in Table 3. According to yet even further particular embodiments, the biomarker panel is represented by the 58 microsatellite regions listed in Table 3.

It is particularly envisaged that this biomarker panel can be used to detect MSI status in cancer. Accordingly, the use of this biomarker panel is provided in the diagnosis of microsatellite instability in cancer.

According to yet other embodiments, a kit is provided for determining MSI in a tumor sample, comprising the tools to genotype the biomarker panel (i.e. the at least eight microsatellite regions selected from those present in 5' UTR or 3' UTR regions from the genes listed in Table 1 and those present in the exons of the genes listed in Table 2). Most particularly, the kit will be adapted to the particularly envisaged biomarker panel(s).

(a) The MSH6/MSH2 complex is involved in the recognition of insertion-deletions loops (IDLs) of one or two bases, which typically occur in homopolymers, whereas the MSH3/MSH2 complex is responsible for the recognition of longer IDLs, which often accumulate in microsatellites. Adapted from Martin et al[54]. (b) The genome-wide somatic mutation rate in the MMR-deficient (MMR−) hypermutator is drastically increased relative to the average somatic mutation rate of two MMR-proficient (MMR+) tumors (3.3E−05 versus 1.6E−06 somatic mutations per basepair or mbp, respectively). (c) The fraction of somatic mutations observed in microsatellites, homopolymers, short homopolymers and non-repeat regions in the MMR-deficient hypermutator is shown, as well as the expected fraction of mutations affecting these regions. Significant differences (P<10E−6) were observed for homopolymers, short homopolymers and non-repeat regions. (d) The fraction of somatic indels observed in microsatellites, homopolymers, short homopolymers and non-repeat regions relative to the expected fraction of mutations in these regions. Significant differences (P<10E−6) were observed for homopolymers, short homopolymers and non-repeat regions. (e) Fraction of somatic substitutions observed in microsatellites, homopolymers, short homopolymers and non-repeat regions relative to the expected fraction of mutations in these regions. Significant differences (P<10E−6) were observed for homopolymers, short homopolymers and non-repeat regions.

Figure 2:
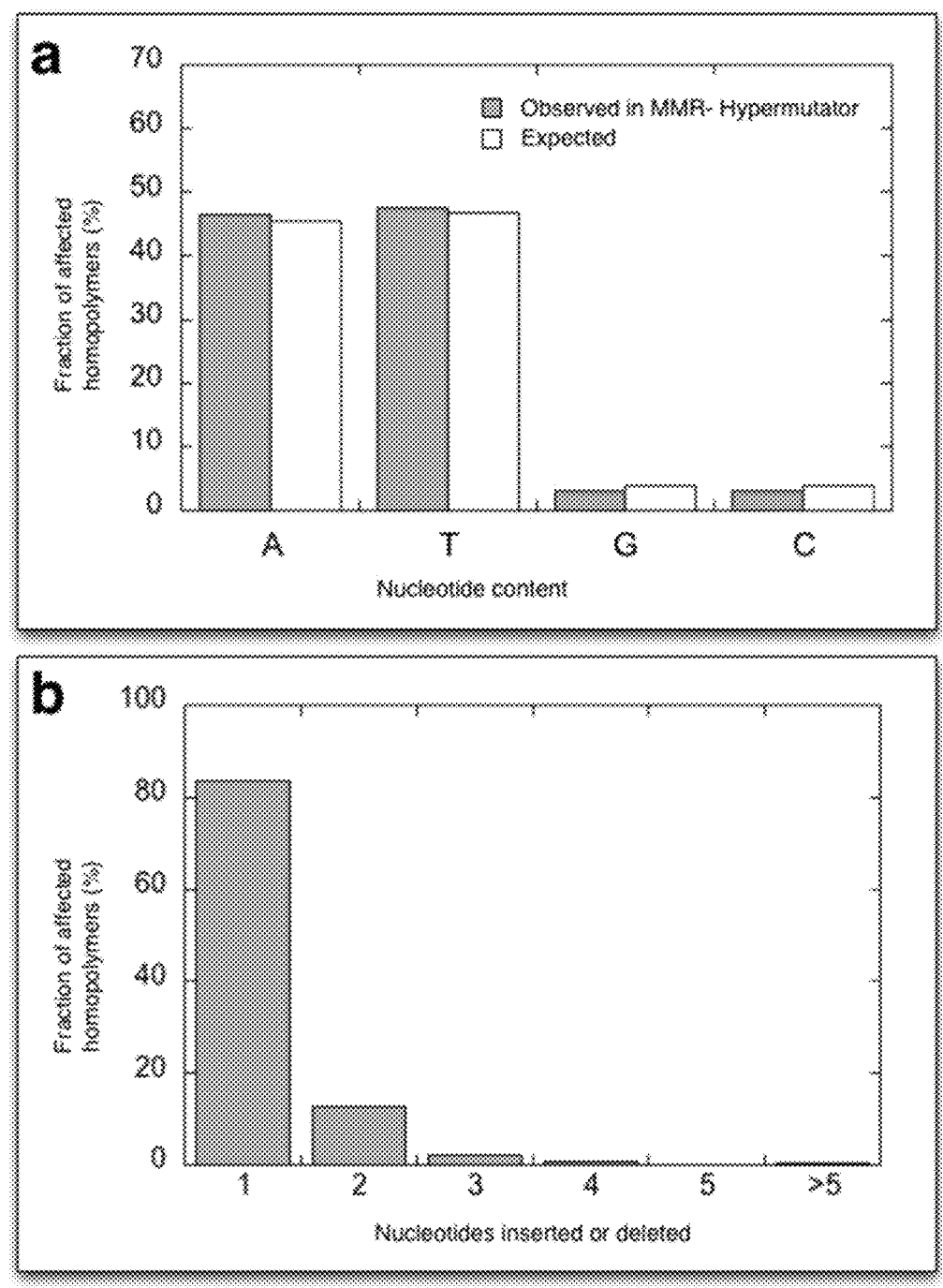

FIG. 2. Somatic indel pattern in the MMR-deficient hypermutator.

(a) The base composition of all homopolymers affected by a somatic indel in the hypermutator is shown relative to the expected number based on genome-wide nucleotide content. Homopolymers consisting of C or G nucleotides were equally prone to accumulate indels. (b) The fraction of homopolymers affected by a somatic indel in function of the number of deleted or inserted bases is shown for the hypermutator. Indels mainly involve one or two basepair indels.

Figure 3:
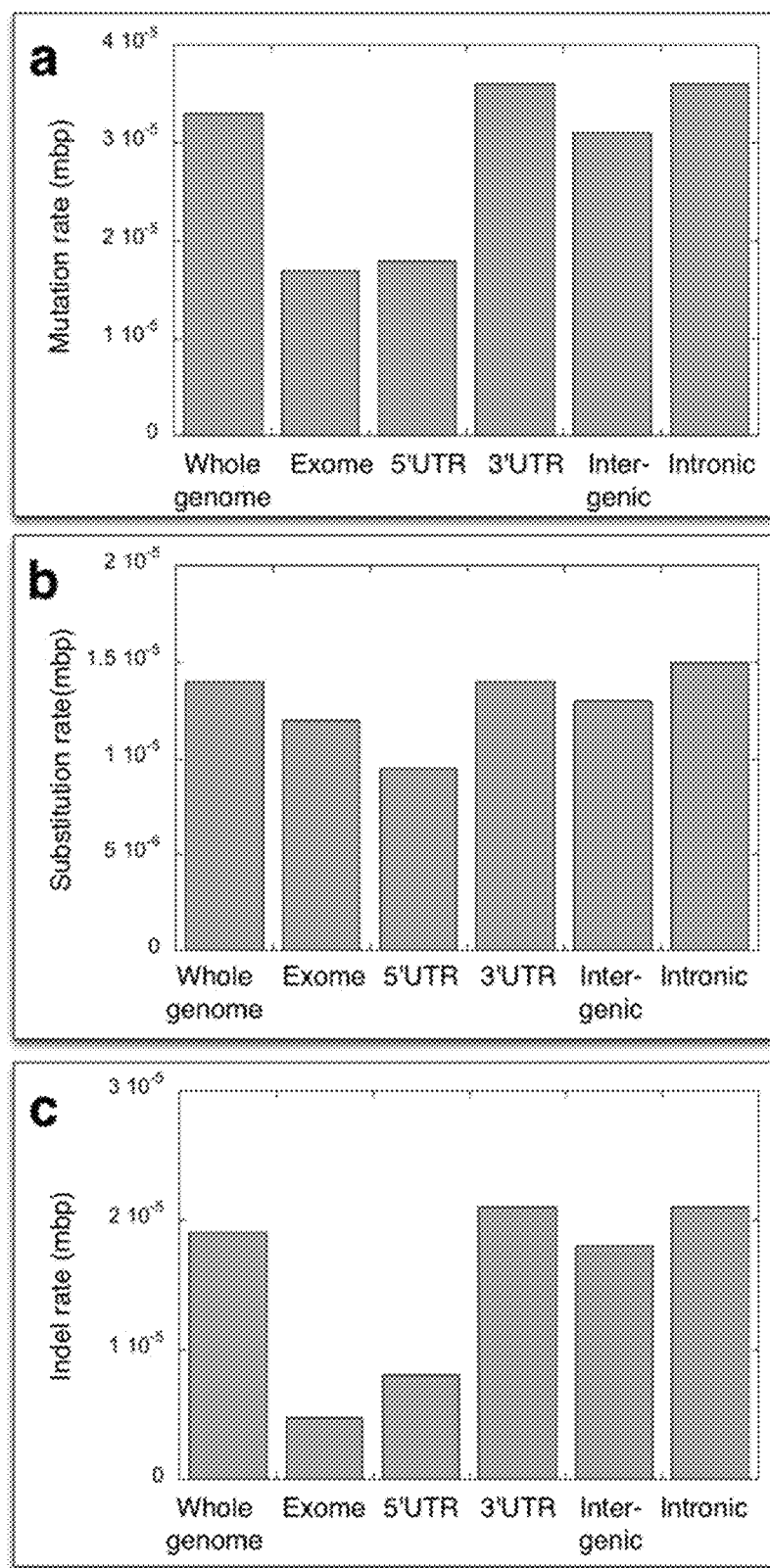

FIG. 3. Negative clonal selection in the exomes of MMR− tumors.

(a) Somatic mutation rates in the hypermutator stratified for exonic, 5'UTR, 3'UTR, intergenic and intronic regions. Mutation rates in the exome were lowest. (b) Somatic substitution rates in the hypermutator stratified into exonic, 5'UTR, 3'UTR, intergenic and intronic regions. The decrease in the number of substitutions was most pronounced in the exome of the hypermutator. (c) Somatic indel rates in the hypermutator stratified into exonic, 5'UTR, 3'UTR, intergenic and intronic regions. The decrease in indels was most pronounced in the exome of the hypermutator.

Figure 4:
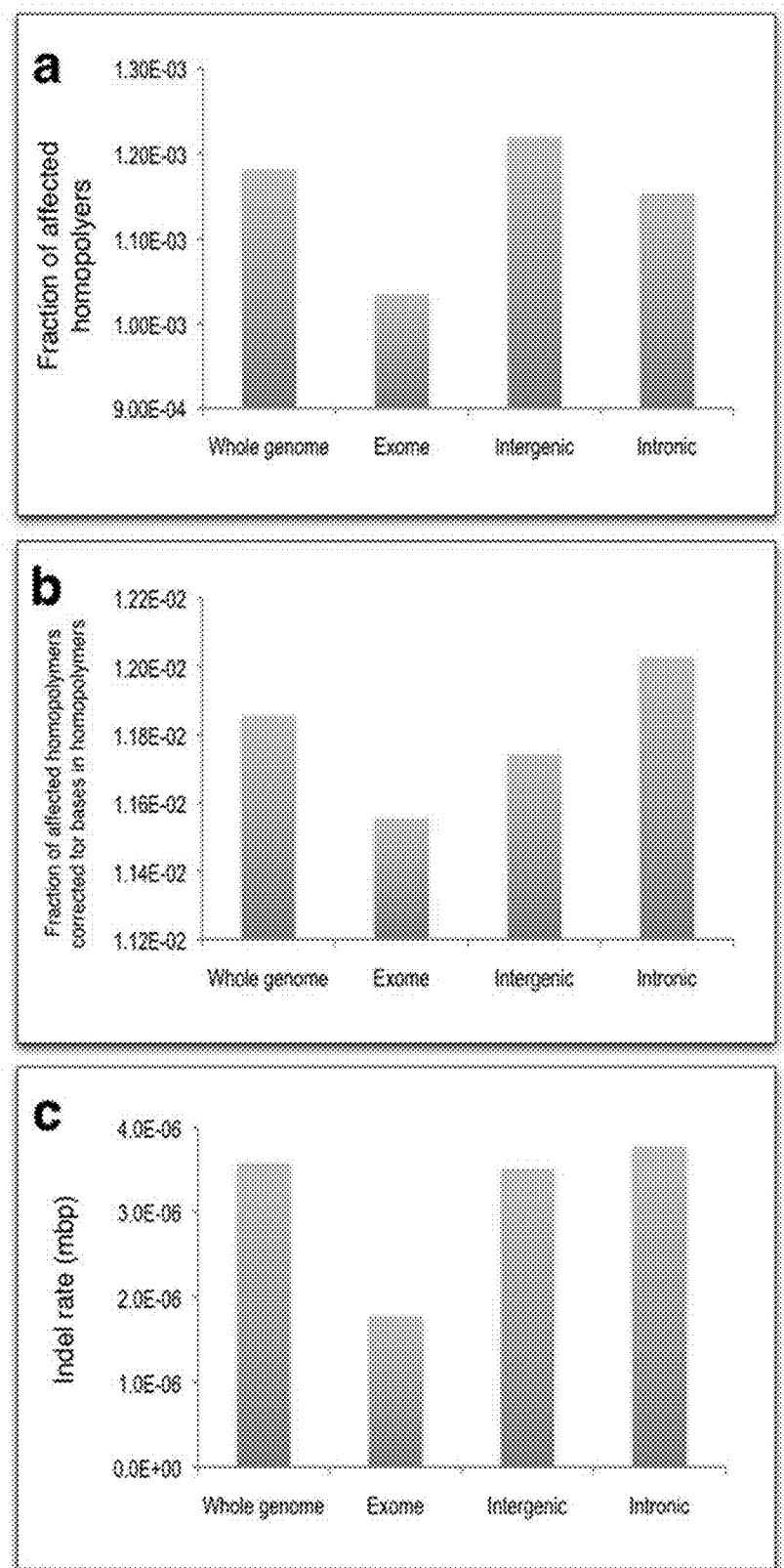

FIG. 4. Indel mutation rate in the whole genome compared to exonic, intergenic and intronic regions.

A, normalized for fraction of affected homopolymers in a given region. B, normalized for the number of bases in homopolymers in the different genomic regions. C, Indel mutation rate in the whole genome compared to exonic, intergenic and intronic regions normalized for fraction of affected homopolymers in a given region for homopolymers of length 6.

Figure 5:
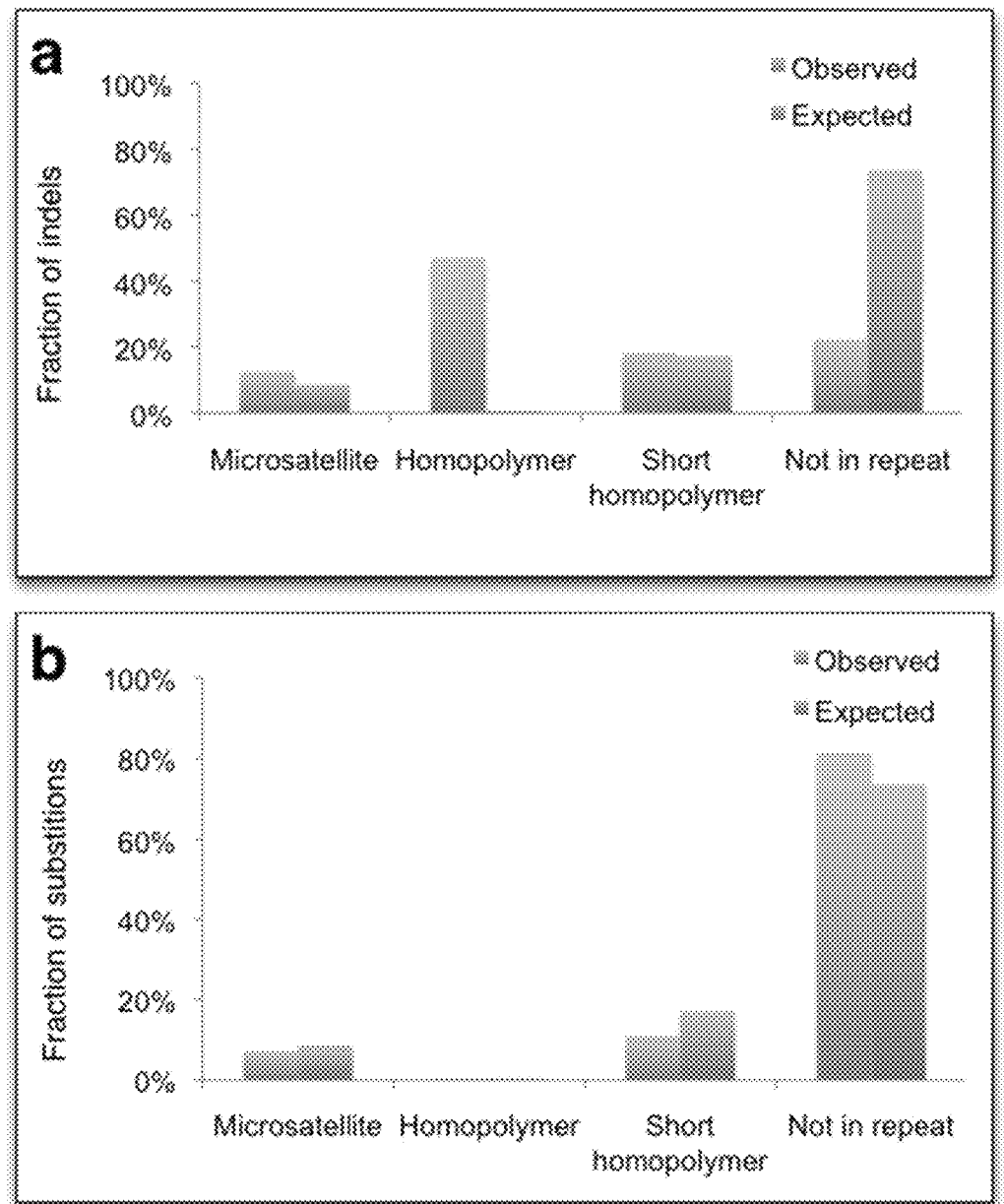

FIG. 5. Fraction of mutations classified by type of repeat region, compared to distribution of repeat regions in the exome.

A, for indels. B, for substitutions.

Figure 6:
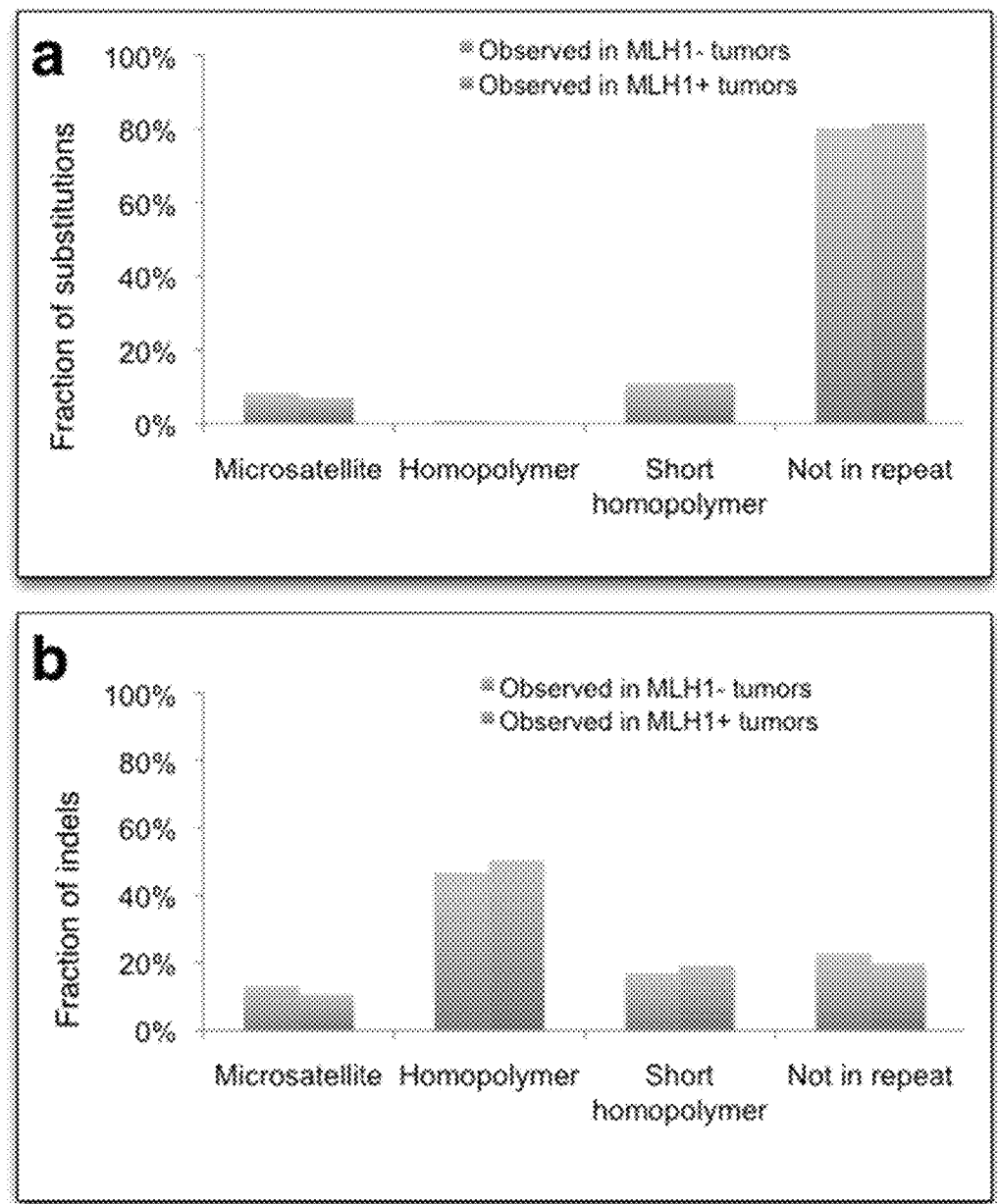

FIG. 6. Fraction of mutations classified by type of repeat region in MLH1– and MLH1+ tumors.

A, for substitutions. B, for indels.

Figure 7:
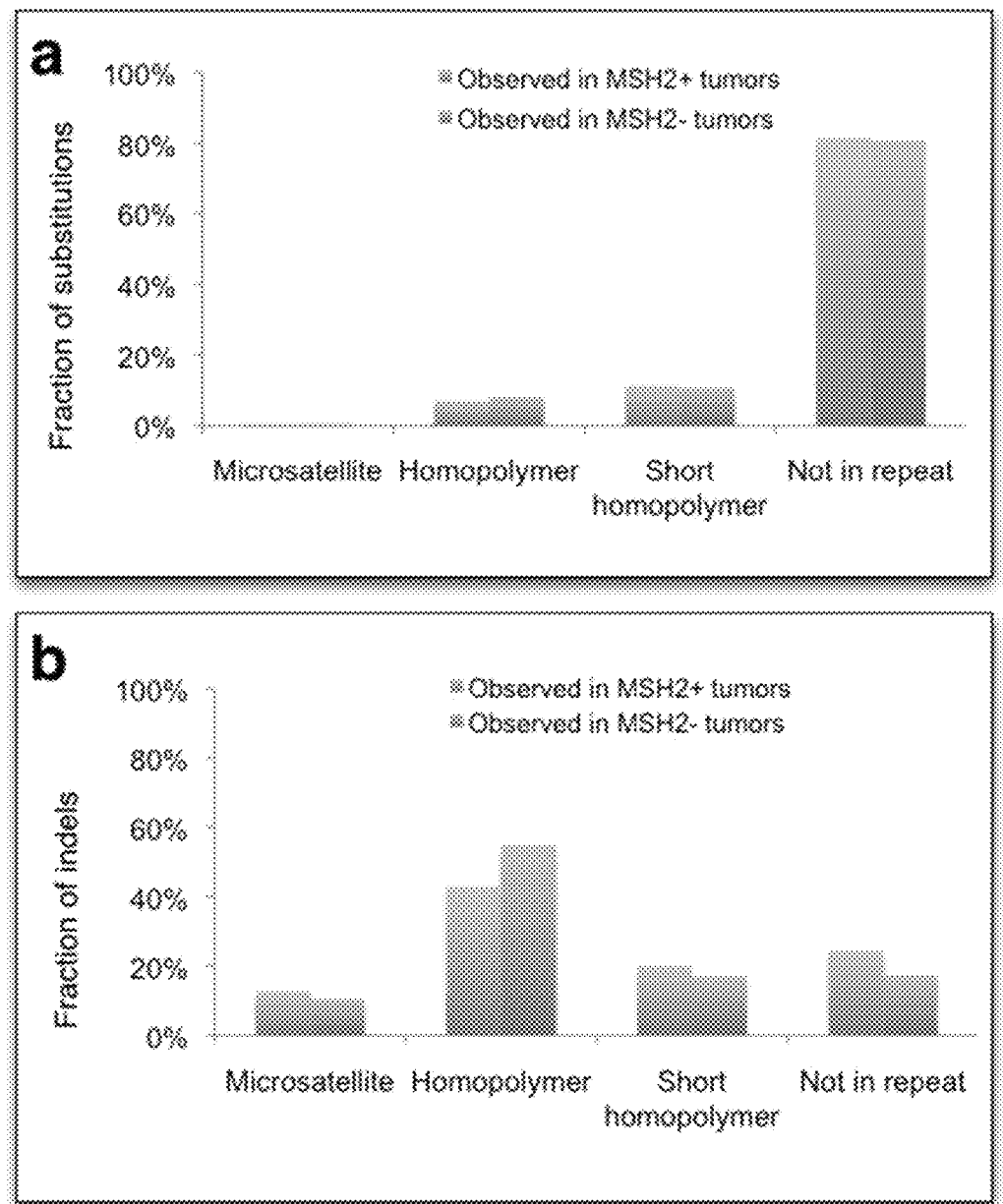

FIG. 7. Fraction of mutations classified by type of repeat region in MSH2– and MSH2+ tumors.

A, for substitutions. B, for indels.

Figure 8:
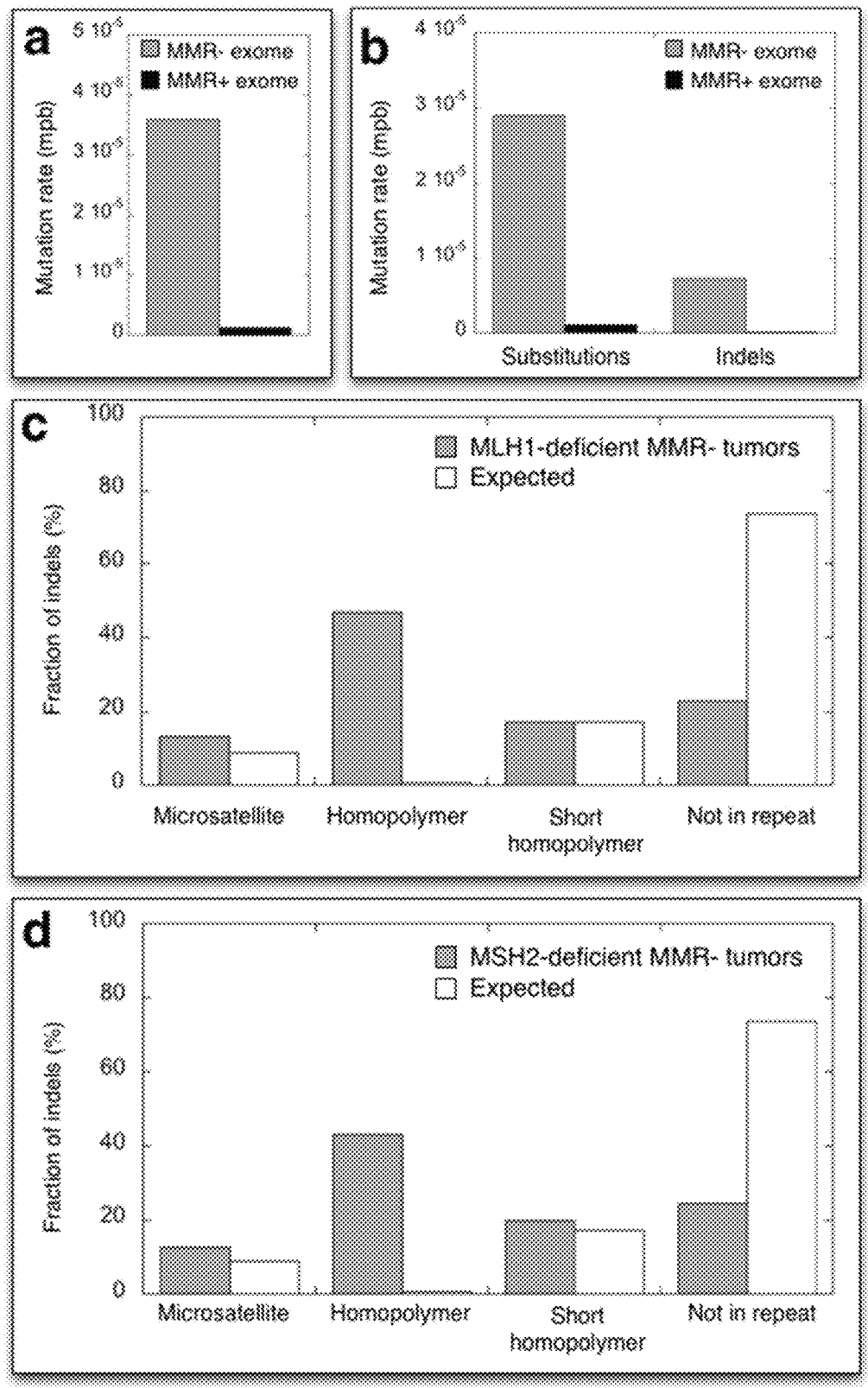

FIG. 8. Positive clonal selection in the exomes of MMR– tumors.

(a) Average somatic mutation rate in the exomes of 7 MMR– versus 4 MMR+ tumors (3.6E–05 versus 1.2E–06 mutations per basepair, respectively). (b) Average mutation rate in the exomes of 7 MMR– versus 4 MMR+ tumors stratified for substitutions and indels. Mutation rates in the hypermutator were much lower for indels than for substitutions in MMR-deficient tumors. (c) The fraction of somatic indels observed in microsatellites, homopolymers, short homopolymers and non-repeat regions in MLH1-deficient MMR– tumors is shown, as well as the expected fraction of mutations affecting these regions. Significant differences (P<10E–6) were observed for homopolymers and non-repeat regions. (d) The fraction of somatic indels observed in microsatellites, homopolymers, short homopolymers and non-repeat regions in MSH2-deficient tumors is shown, as well as the expected fraction of mutations affecting these regions. Significant differences (P<10E–6) were observed for homopolymers and non-repeat regions.

Figure 9:
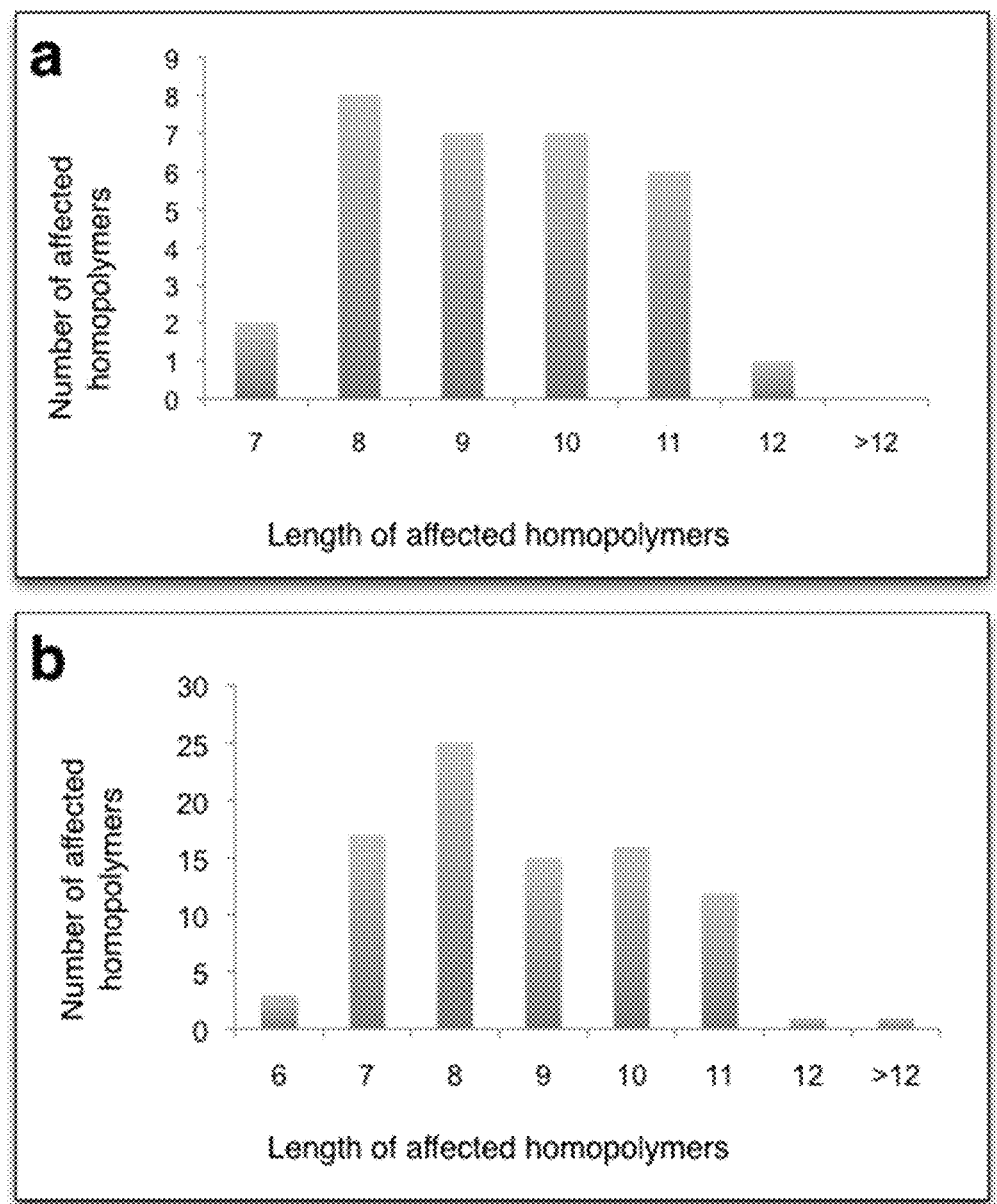

FIG. 9. Analysis of recurrently affected homopolymers.

A, Number of affected homopolymers plotted versus length of affected homopolymer for homopolymers affected in at least 3 out of 8 MMR– tumors. B, Number of affected homopolymers plotted versus length of affected homopolymer for homopolymers affected in at least 2 out of 8 MMR-tumors.

Figure 10:
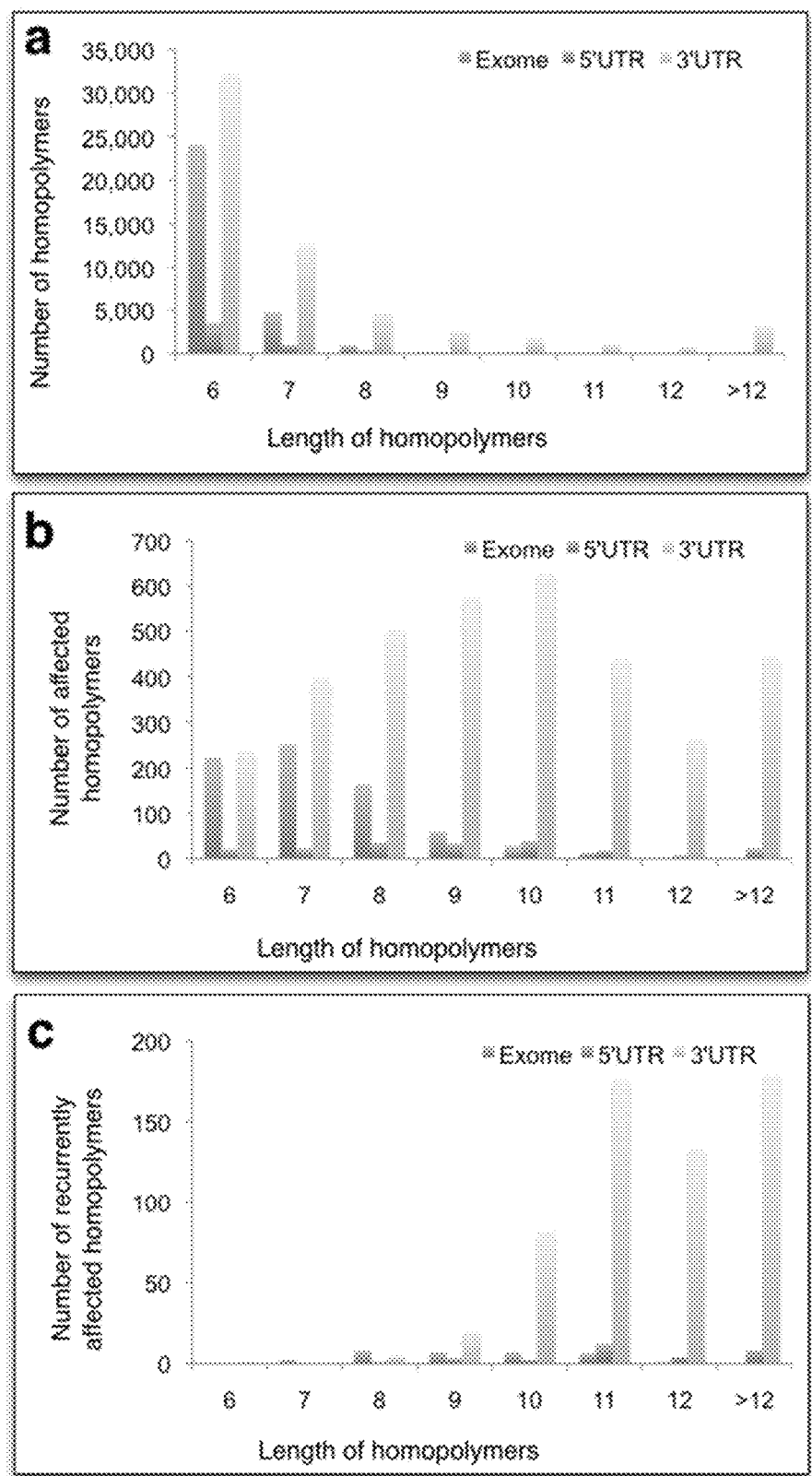

FIG. 10. Homopolymer length and recurrence of somatic mutations in exonic regions, 5' UTRs and 3' UTRs A, Number of homopolymers versus length of homopolymers for all homopolymers in exome, 5' UTR and 3' UTR regions. B, Number of affected homopolymers in MMR deficient tumors versus length of homopolymers in exome, 5' UTR and 3' UTR regions. C, Number of recurrently affected homopolymers in MMR deficient tumors versus length of homopolymers in exome, 5' UTR and 3' UTR regions.

Figure 11:
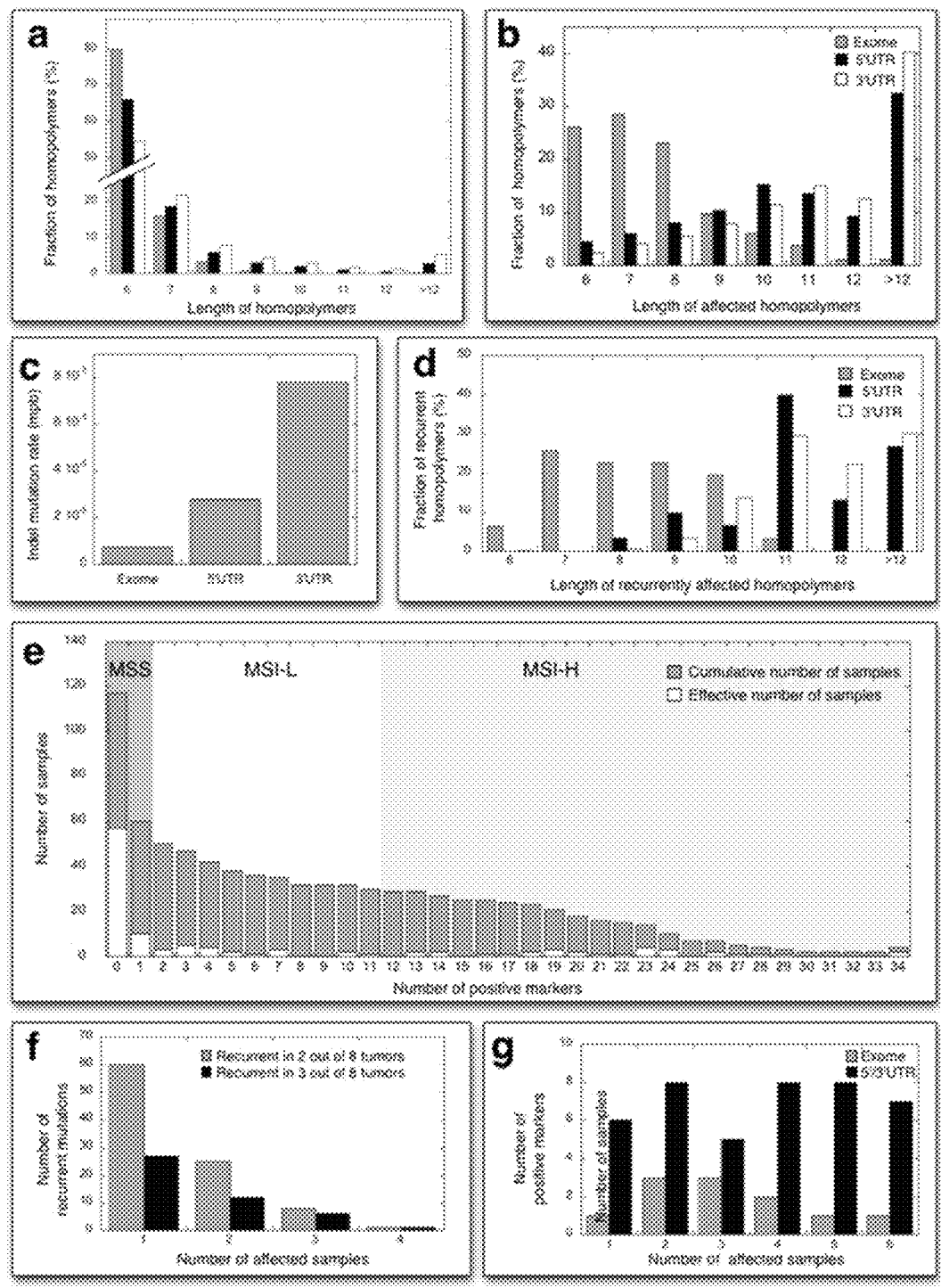

FIG. 11. Patterns of recurrent indels and substitutions in the exome, 5' and 3'UTR of MMR– tumors.

(a) The fraction of homopolymers in function of the homopolymer length is shown for exonic, 5' and 3'UTRs. Data were calculated based on the captured regions in the hg19 reference genome (respectively 83.9% and 91.9% of the 5' and 3' UTR regions). (b) Average somatic indel rate in the exome, 5' and 3'UTR of 7 MMR– tumors. Indel mutation rates of the 3'UTR and to a lesser extent also of the 5'UTR were higher than in the exome. (c) The fraction of homopolymers affected by a somatic indels in function of the homopolymer length is shown for exonic, 5' and 3'UTRs. Affected homopolymers in the exome mainly had a length between 6 and 8 nucleotides, whereas affected homopolymers in the 5' and 3'UTRs were mainly affected by longer homopolymers. (d) The fraction of homopolymers recurrently affected by a somatic indels in function of the homopolymer length is shown for exonic, 5' and 3'UTRs. Affected homopolymers in the exome mainly exhibited a length between 8 and 11 nucleotides, whereas affected homopolymers in the 5' and 3'UTRs were generally affected by longer (>11) homopolymers. (e) A panel of 58 recurrent indels selected from exonic, 5'UTR and 3'UTR regions was applied to an independent series of 117 unselected primary endometrial tumors to assess MSI. A continuous spectrum of MSI, ranging from 12 to 34 positive markers (MSI-H or high MSI), 2 to 11 positive markers (MSI-L or low MSI) and 0 to 1 positive marker (microsatellite stable or MSS) was observed in respectively 24.8%, 17.9% and 57.3% of tumors. (f) Recurrent mutations affecting 2 (grey columns), respectively 3 (black columns) out of 8 endometrial MMR– tumors are also present in 3 MMR– leukemia and 1 MMR– ovarian tumor. (g) Our panel of 58 recurrent indels was applied to 9 colorectal tumors with known MSI and MMR-deficiency. The minimal number of positive markers per sample was 31 in these samples, indicating that all tumors were categorized as MSI-H by our panel. The maximum number of positive markers for one sample was 36 out of 58 markers. For the 58 tested markers, between 0 and 6 samples were positive, with the majority of the markers (66%) positive for 3 or more samples. In general, more 5' and 3'UTR markers than exonic markers were affected in the colorectal samples.

DETAILED DESCRIPTION

Definitions

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. Unless specifically defined herein, all terms used herein have the same meaning as they would to one skilled in the art of the present invention. Practitioners are particularly directed to Sambrook et al., Molecular Cloning: A Laboratory Manual, 2$^{nd}$ ed., Cold Spring Harbor Press, Plainsview, N.Y. (1989); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

The term "microsatellite" or "microsatellite regions" as used herein refers to mono-, di-, tri-, tetra, penta- or hexa-nucleotide repeats in a nucleotide sequence, consisting of at least two repeat units and with a minimal length of 6 bases. A particular subclass of microsatellites includes the homopolymers. "Homopolymer" as used herein refers to a microsatellite region that is a mononucleotide repeat of at least 6 bases; in other words a stretch of at least 6 consecutive A, C, T or G residues if looking at the DNA level. Most particularly, when determining microsatellites, one looks at genomic DNA of a subject (or of genomic DNA of a cancer present in the subject).

The term "MSI status" as used in the application refers to the presence of microsatellite instability (MSI), a clonal or somatic change in the number of repeated DNA nucleotide units in microsatellites. MSI status can be one of three discrete classes: MSI-H, also referred to as MSI-high, MSI positive or MSI, MSI-L, also referred to as MSI-low, or microsatelitte stable (MSS), also referred to as absence of MSI. Typically, to be classified as MSI-H, at least 20% of the markers used to classify MSI status need to score positive, while for the MSS classification, less than 2.5% score positive. If an intermediate number of markers scores positive, the tumor is classified as MSI-L. Alternatively, only the difference between presence and absence of microsatellite instability is assessed, in which case the status is either presence of MSI or absence of MSI (=MSS).

An "indel" as used herein refers to a mutation class that includes both insertions, deletions, and the combination thereof. An indel in a microsatellite region results in a net gain or loss of nucleotides. The presence of an indel can be established by comparing it to DNA in which the indel is not present (e.g. comparing DNA from a tumor sample to germline DNA from the subject with the tumor), or, especially in case of monomorphic microsatellites or homopolymers, by comparing it to the known length of the microsatellite, particularly by counting the number of repeated units. A "monomorphic microsatellite" is one in which all individuals, particularly all individuals of a given population, share the same number of repeat units. This in contrast to a "polymorphic microsatellite", which is used to refer to microsatellites in which more than 1% of a given population display heterozygosity for the number of repeat units. By way of example, the BAT26 marker is comprised of 26 adenines in more than 99% of ethnic Europeans, whereas alleles with different numbers of adenines at this location (eg, 15, 20, 22, 23) are seen in up to 25% of ethnic Africans, including African Americans[17]. Thus, BAT26 is a monomorphic microsatellite in Europeans and a polymorphic microsatellite in Africans[16]

A "sample of tumor DNA" refers to any sample that can be used as basis for sequencing, wherein DNA from a cancer is present. The term "cancer" as used herein, refers to different diseases involving unregulated cell growth, also referred to as malignant neoplasm. The term "tumor" is used as a synonym in the application. It is envisaged that this term covers all solid tumor types (carcinoma, sarcoma, blastoma), but it also explicitly encompasses non-solid cancer types such as leukemia. Thus, a "sample of tumor DNA" can also be a blood sample from a person with leukemia. Typically, a sample of tumor DNA has at one point been isolated from a subject, particularly a subject with cancer. Optionally, it has undergone one or more forms of pre-treatment (e.g. lysis, fractionation, separation, purification) in order for the DNA to be sequenced, although it is also envisaged that DNA from an untreated sample is sequenced. As used herein, the noun "subject" refers to an individual vertebrate, more particularly an individual mammal, most particularly an individual human being. A "subject" as used herein is typically a human, but can also be a mammal, particularly domestic animals such as cats, dogs, rabbits, guinea pigs, ferrets, rats, mice, and the like, or farm animals like horses, cows, pigs, goat, sheep, llamas, and the like. A subject can also be a non-mammalian vertebrate, like a fish, reptile, amphibian or bird; in essence any animal which can develop cancer fulfills the definition.

The term "Lynch syndrome" as used herein refers to an autosomal dominant genetic condition which has a high risk of colon cancer as well as other cancers including endometrium, ovary, stomach, small intestine, hepatobiliary tract, upper urinary tract, brain, and skin cancer. The increased risk for these cancers is due to inherited mutations that impair DNA mismatch repair. The old name for the condition is HNPCC.

DNA replication errors occurring in mismatch repair (MMR) deficient cells persist as mismatch mutations and predispose to a range of tumors. Here, the first genomes from MMR-deficient tumors were sequenced, allowing the unbiased assessment of DNA replication errors. It was observed that mutation rates were drastically increased relative to MMR-proficient tumors. Insertion or deletion (indel) mutations occurred most frequently and were largely confined to homopolymer stretches, whereas single basepair substitutions mainly consisted of A:T>G:C and G:C>A:T transitions and were more often located nearby indels. As the rates of substitutions were higher nearby somatic indels, this suggests that indel mutations act as mutagenic sites during DNA replication. Due to negative clonal selection, somatic mutation rates were lower in the exome than the rest of the genome, whereas due to positive selection, some exonic mutations occurred in several MMR-deficient tumors. These recurrent mutations specifically affected genes expressed in the normal matched tissue, suggesting that they represent drivers of MMR-deficient tumor progression.

Intriguingly, indels were mainly located in homopolymers, in particular in homopolymers of increased length. These observations also have an immediate clinical implication. The extended Bethesda panel, currently used for the diagnostic classification of MSI tumors[9,14-15] has only limited sensitivity, i.e., 80%, 84% and 55% for MLH1-, MSH2- and MSH6-deficient tumors[16], presumably because this panel consists of 8 microsatellite and only 2 homopolymer markers, respectively with a length of 25 and 26 nucleotides. By applying our panel of 58 recurrent indels to 117 endometrial tumors, we could demonstrate that up to 42.7% of tumors exhibited a highly variable degree of MSI. This was significantly higher than previously reported, most likely because these indels were not randomly selected, but were identified through an unbiased assessment of mutations recurrently affecting the exome, 5' and 3'UTRs. We also observed that recurrent indels in endometrial tumors were located in MMR− tumors of other cancer types. Since indels in 3'UTRs are only determined by the length of the affected homopolymer, whereas in the exome they need to be positively selected in genes expressed by the tissue of origin, most indels shared among various cancer types were located in 5' and 3'UTRs. Therefore, recurrent mutations in 5' and 3'UTRs or other non-coding sequences seem to be particularly suitable to detect MSI across various cancer types. Interestingly, a selective panel of the most recurrent mutations was highly sensitive to detect microsatellite instability (MSI) in various cancer types. In 117 primary endometrial tumors, a continuous spectrum of MSI was observed in almost half of the tumors, suggesting that MSI occurs more frequently than anticipated.

As will be detailed in the Examples section, particularly in Example 6, there are particular homopolymers in 5'UTR and 3'UTR regions that are more frequently affected by indels in MMR-deficient tumors. A list of the most frequent recurrently mutated genes is provided in Table 1.

TABLE 1

Most common recurrent indels in 5' and 3'UTR regions for 8 MMR-deficient tumor samples.

| Nr of affected samples | Gene | Chromosome | Start Position | Affected homopolymer base | Affected homopolymer length | Region |
|---|---|---|---|---|---|---|
| 7 | ARHGEF11 | chr1 | 157014811 | A | 12 | 5' UTR |
| 6 | LRMP | chr12 | 25205380 | A | 11 | 5' UTR |
| 5 | GABRG2 | chr5 | 161494990 | A | 12 | 5' UTR |
| 5 | MBNL1 | chr3 | 152017897 | T | 11 | 5' UTR |
| 4 | ARHGEF9 | chrX | 62974288 | T | 12 | 5' UTR |
| 4 | CCT6B | chr17 | 33288433 | A | 11 | 5' UTR |
| 4 | EPHB6 | chr7 | 142560576 | A | 13 | 5' UTR |
| 4 | GRIA2 | chr4 | 158142151 | A | 9 | 5' UTR |
| 4 | LMOD3 | chr3 | 69171664 | T | 13 | 5' UTR |
| 4 | NDE1 | chr16 | 15737427 | T | 11 | 5' UTR |
| 4 | OMD | chr9 | 95179844 | T | 11 | 5' UTR |
| 4 | TMEM177 | chr2 | 120437061 | A | 11 | 5' UTR |
| 4 | TRPS1 | chr8 | 116681041 | A | 14 | 5' UTR |
| 4 | ZNF781 | chr19 | 38161161 | T | 11 | 5' UTR |
| 4 | ZXDA | chrX | 57936946 | A | 9 | 5' UTR |
| 3 | AMD1 | chr6 | 111196178 | A | 11 | 5' UTR |
| 3 | ASPH | chr8 | 62602295 | A | 11 | 5' UTR |
| 3 | BMP5 | chr6 | 55739711 | A | 14 | 5' UTR |
| 3 | CBLN2 | chr18 | 70211389 | A | 14 | 5' UTR |
| 3 | CEPT1 | chr1 | 111690319 | A | 9 | 5' UTR |
| 3 | EBF1 | chr5 | 158526596 | T | 11 | 5' UTR |
| 3 | ESCO1 | chr18 | 19164371 | A | 11 | 5' UTR |
| 3 | KDM2B | chr12 | 122018157 | G | 10 | 5' UTR |
| 3 | LRRC70 | chr5 | 61874619 | A | 18 | 5' UTR |
| 3 | MCF2 | chrX | 138724841 | A | 15 | 5' UTR |
| 3 | MEIS1 | chr2 | 66662690 | T | 13 | 5' UTR |
| 3 | MEIS2 | chr15 | 37391752 | T | 12 | 5' UTR |
| 3 | SEMA6A | chr5 | 115910134 | A | 11 | 5' UTR |
| 3 | SETBP1 | chr18 | 42260910 | G | 8 | 5' UTR |
| 3 | ST7L | chr1 | 113162029 | C | 10 | 5' UTR |
| 7 | MAPK1IP1L | chr14 | 55535728 | T | 13 | 3' UTR |
| 7 | NARG2 | chr15 | 60712503 | T | 13 | 3' UTR |
| 7 | PI15 | chr8 | 75766071 | T | 10 | 3' UTR |
| 6 | AHCYL1 | chr1 | 110566210 | A | 14 | 3' UTR |
| 6 | APH1B | chr15 | 63600287 | T | 12 | 3' UTR |
| 6 | C17orf63 | chr17 | 27083744 | T | 12 | 3' UTR |
| 6 | CALN1 | chr7 | 71245682 | A | 12 | 3' UTR |
| 6 | CCND2 | chr12 | 4410638 | T | 16 | 3' UTR |
| 6 | CD5L | chr1 | 157801230 | A | 13 | 3' UTR |
| 6 | CEP170 | chr1 | 243288181 | T | 11 | 3' UTR |
| 6 | CREB3L2 | chr7 | 137561927 | A | 11 | 3' UTR |
| 6 | CSNK1G3 | chr5 | 122950254 | T | 13 | 3' UTR |
| 6 | DIDO1 | chr20 | 61536691 | A | 11 | 3' UTR |
| 6 | DRAM2 | chr1 | 111660181 | A | 11 | 3' UTR |
| 6 | EIF4G3 | chr1 | 21133496 | T | 13 | 3' UTR |
| 6 | FAM38B | chr18 | 10670849 | T | 14 | 3' UTR |
| 6 | GSK3B | chr3 | 119542766 | A | 11 | 3' UTR |
| 6 | KCNMB4 | chr12 | 70824838 | A | 14 | 3' UTR |
| 6 | KDM5A | chr12 | 389523 | T | 11 | 3' UTR |
| 6 | MYO5B | chr18 | 47351784 | A | 12 | 3' UTR |
| 6 | NEK5 | chr13 | 52639268 | A | 13 | 3' UTR |
| 6 | NPR3 | chr5 | 32787131 | A | 11 | 3' UTR |
| 6 | PPP1R12A | chr12 | 80169697 | T | 13 | 3' UTR |
| 6 | PRTG | chr15 | 55903921 | A | 11 | 3' UTR |
| 6 | RAB11FIP1 | chr8 | 37718707 | A | 13 | 3' UTR |
| 6 | RASGRP1 | chr15 | 38781450 | T | 13 | 3' UTR |
| 6 | SH3KBP1 | chrX | 19552231 | T | 13 | 3' UTR |
| 6 | SHROOM3 | chr4 | 77701305 | A | 12 | 3' UTR |
| 6 | SLC5A3 | chr21 | 35470291 | T | 11 | 3' UTR |
| 6 | UBE2Z | chr17 | 47005701 | A | 11 | 3' UTR |
| 6 | UST | chr6 | 149398012 | T | 13 | 3' UTR |
| 6 | ZNF275 | chrX | 152617043 | A | 12 | 3' UTR |
| 5 | EIF4G3 | chr1 | 21133286 | A | 13 | 3' UTR |
| 5 | FCHSD2 | chr11 | 72549649 | A | 10 | 3' UTR |
| 5 | FMO2 | chr1 | 171178335 | A | 11 | 3' UTR |
| 5 | RYR3 | chr15 | 34157541 | A | 10 | 3' UTR |
| 5 | TMEM65 | chr8 | 125325217 | A | 11 | 3' UTR |
| 5 | WHSC1L1 | chr8 | 38175279 | A | 11 | 3' UTR |
| 4 | ABAT | chr16 | 8876793 | T | 11 | 3' UTR |
| 4 | ARFIP1 | chr4 | 153832103 | T | 11 | 3' UTR |
| 4 | BTBD7 | chr14 | 93708030 | A | 10 | 3' UTR |
| 4 | C15orf2 | chr15 | 24927891 | A | 10 | 3' UTR |
| 4 | CALN1 | chr7 | 71249416 | T | 10 | 3' UTR |

TABLE 1-continued

Most common recurrent indels in 5' and 3'UTR regions for 8 MMR-deficient tumor samples.

| Nr of affected samples | Gene | Chromosome | Start Position | Affected homopolymer base | Affected homopolymer length | Region |
|---|---|---|---|---|---|---|
| 4 | CCDC89 | chr11 | 85395559 | T | 10 | 3' UTR |
| 4 | CCND1 | chr11 | 69466273 | A | 10 | 3' UTR |
| 4 | ENTPD4 | chr8 | 23289680 | A | 11 | 3' UTR |
| 4 | FCHSD2 | chr11 | 72548510 | A | 14 | 3' UTR |
| 4 | FGFBP3 | chr10 | 93666830 | A | 11 | 3' UTR |
| 4 | LANCL1 | chr2 | 211297865 | T | 9 | 3' UTR |
| 4 | PPM1A | chr14 | 60761433 | T | 10 | 3' UTR |
| 4 | PURB | chr7 | 44920830 | A | 9 | 3' UTR |
| 4 | ST7L | chr1 | 113067470 | A | 10 | 3' UTR |
| 4 | SULF2 | chr20 | 46286320 | A | 10 | 3' UTR |
| 4 | TMC7 | chr16 | 19073947 | A | 10 | 3' UTR |
| 4 | TSR2 | chrX | 54471045 | T | 10 | 3' UTR |
| 4 | UBA6 | chr4 | 68481877 | T | 12 | 3' UTR |
| 4 | USP14 | chr18 | 212029 | A | 9 | 3' UTR |
| 4 | ZNF185 | chrX | 152140995 | C | 10 | 3' UTR |
| 4 | ZNF287 | chr17 | 16454419 | T | 9 | 3' UTR |
| 3 | AKIRIN1 | chr1 | 39471673 | A | 10 | 3' UTR |
| 3 | ARL10 | chr5 | 175800427 | T | 10 | 3' UTR |
| 3 | BMPR2 | chr2 | 203426176 | T | 8 | 3' UTR |
| 3 | C17orf96 | chr17 | 36829265 | T | 8 | 3' UTR |
| 3 | CCND2 | chr12 | 4409520 | T | 10 | 3' UTR |
| 3 | EDEM1 | chr3 | 5260540 | T | 10 | 3' UTR |
| 3 | FOXN2 | chr2 | 48604358 | T | 10 | 3' UTR |
| 3 | FOXN2 | chr2 | 48603079 | T | 10 | 3' UTR |
| 3 | HDAC4 | chr2 | 239974109 | A | 9 | 3' UTR |
| 3 | HUS1B | chr6 | 656079 | A | 10 | 3' UTR |
| 3 | KDM5A | chr12 | 393804 | T | 11 | 3' UTR |
| 3 | KIF5C | chr2 | 149879665 | T | 10 | 3' UTR |
| 3 | LRCH1 | chr13 | 47325657 | A | 10 | 3' UTR |
| 3 | MKLN1 | chr7 | 131175980 | A | 10 | 3' UTR |
| 3 | PCDHB3 | chr5 | 140482943 | T | 10 | 3' UTR |
| 3 | RYBP | chr3 | 72424549 | T | 9 | 3' UTR |
| 3 | SH3KBP1 | chrX | 19553810 | T | 12 | 3' UTR |
| 3 | SLC35F1 | chr6 | 118638703 | A | 8 | 3' UTR |

Of note, some of the genes listed in Table 1 have more than one recurrent indel in the UTR regions (e.g. CALN1, EIF4G3, KDM5A), which increases the likelihood that these genomic regions are not randomly affected, but underwent positive selection.

Importantly, also homopolymers in exonic regions are more frequently affected by indels in MMR-deficient tumors. As explained in e.g. Example 5, this is not based on sequence length, but due to positive clonal selection. So although typically less frequently recurrently mutated, these mutations might be drivers of tumor progression. A list of the 31 genes most frequently affected with indels in their exonic regions is provided in Table 2.

TABLE 2

Most common recurrent indels in exons for 8 MMR-deficient tumor samples.

| Nr of affected samples | Gene | Chromosome | Start Position | Affected homopolymer base | Affected homopolymer length | Known Cancer Gene | Affected in HMR deficient tumors |
|---|---|---|---|---|---|---|---|
| 6 | MSH6 | chr2 | 48030639 | C | 8 | x | x |
| 6 | SETD1B | chr12 | 122242657 | C | 8 | | |
| 5 | CASP5 | chr11 | 104879686 | T | 10 | | x |
| 5 | RBMXL1 | chr1 | 89449508 | T | 11 | | |
| 5 | SEC31A | chr4 | 83785564 | T | 9 | | |
| 4 | CCDC150 | chr2 | 197531518 | A | 11 | | |
| 4 | PHF2 | chr9 | 96422611 | A | 8 | x | |
| 4 | RPL22 | chr1 | 6257784 | T | 8 | x | |
| 4 | TMEM60 | chr7 | 77423459 | T | 9 | | |
| 3 | AIM2 | chr1 | 159032486 | T | 10 | | x |
| 3 | ASTE1 | chr3 | 130733046 | T | 11 | | x |
| 3 | CASP5 | chr11 | 104878040 | T | 10 | x | x |
| 3 | CTCF | chr16 | 67645338 | A | 7 | x | |
| 3 | DDX27 | chr20 | 47858503 | A | 8 | | |
| 3 | EXOSC9 | chr4 | 122723893 | T | 8 | | |
| 3 | FAM111B | chr11 | 58892376 | A | 10 | | |
| 3 | GRIK2 | chr6 | 102503431 | A | 8 | x | |

TABLE 2-continued

Most common recurrent indels in exons for 8 MMR-deficient tumor samples.

| Nr of affected samples | Gene | Chromosome | Start Position | Affected homopolymer base | Affected homopolymer length | Known Cancer Gene | Affected in HMR deficient tumors |
|---|---|---|---|---|---|---|---|
| 3 | KIAA0182 | chr16 | 85682289 | C | 8 | | |
| 3 | KIAA1919 | chr6 | 111587360 | T | 9 | | |
| 3 | MLL3 | chr7 | 151874147 | T | 9 | x | |
| 3 | MYL1 | chr2 | 211179765 | T | 11 | x | |
| 3 | OR7E24 | chr19 | 9361740 | T | 11 | | |
| 3 | P4HTM | chr3 | 49043192 | C | 7 | | |
| 3 | PRKDC | chr8 | 48866909 | T | 10 | | x |
| 3 | PRRT2 | chr16 | 29825015 | C | 9 | | |
| 3 | RNPC3 | chr1 | 104076466 | A | 12 | | |
| 3 | SMC6 | chr2 | 17898125 | T | 9 | x | |
| 3 | TAF1B | chr2 | 9989570 | A | 11 | | x |
| 3 | TMEM97 | chr17 | 26653806 | A | 10 | | |
| 3 | TTK | chr6 | 80751896 | A | 9 | | x |
| 3 | UVRAG | chr11 | 75694430 | A | 10 | | x |

As detailed in the Examples section, and shown in FIG. 11E, over 50% of markers taken from Table 1 score positive in a random set of MMR-deficient tumors, while this is also the case for over a third of the exonic markers listed in Table 2. This allows to correctly classify the MMR deficient tumor as MSI positive with high accuracy and certainty.

Accordingly, methods are provided of diagnosing MSI status of a tumor, comprising determining the presence of an indel in at least two microsatellite regions in a sample of the tumor DNA, wherein the at least two microsatellite regions are at least two microsatellite regions present in 5' UTR or 3' UTR regions from the genes listed in Table 1, or at least three microsatellite regions selected from those present in the exons of the genes listed in Table 2 and/or present in 5' UTR or 3' UTR regions from the genes listed in Table 1, wherein the presence of at least one indel is indicative of MSI.

Particularly, the microsatellite regions are homopolymer regions. They are most particularly identical to the homopolymer regions listed in Table 1 or 2.

It is particularly envisaged to use several markers, as this increases the power of MSI classification and increases sensitivity. Particularly, a mix of UTR markers from Table 1 and exonic markers from Table 2 is used. Several markers may be at least 2 from each list, but the total number of markers particularly is at least 5, at least 8, at least 10, at least 12, at least 15, at least 20.

A biomarker panel consisting of a selection of 58 markers taken from Table 1 and 2 was designed (see Examples section). According to particular embodiments, these markers are used for diagnosing MSI status. These 58 markers are listed in Table 3.

TABLE 3

Panel of 58 markers.

| Marker Nr. | Gene | Region | Type | Chromosome | Position | Reference base |
|---|---|---|---|---|---|---|
| 1 | DDX27 | Exonic | Deletion | 20 | 47858504 | A |
| 2 | EXOSC9 | Exonic | Deletion | 4 | 122723894 | T |
| 3 | FAM111B | Exonic | Deletion | 11 | 58892377 | A |
| 4 | GRIK2 | Exonic | Deletion | 6 | 102503432 | A |
| 5 | KIAA1919 | Exonic | Deletion | 6 | 111587361 | T |
| 6 | MSH6 | Exonic | Insertion/Deletion | 2 | 48030638 | C |
| 7 | MYL1 | Exonic | Deletion | 2 | 211179766 | T |
| 8 | PHF2 | Exonic | Deletion | 9 | 96422612 | A |
| 9 | SEC31A | Exonic | Deletion | 4 | 83785565 | T |
| 10 | SETD1B | Exonic | Deletion | 12 | 122242658 | C |
| 11 | TMEM60 | Exonic | Deletion | 7 | 77423460 | T |
| 12 | TTK | Exonic | Deletion | 6 | 80751897 | A |
| 13 | ABAT | 3'UTR | Deletion | 16 | 8876793 | T |
| 14 | AKIRIN1 | 3'UTR | Deletion | 1 | 39471673 | A |
| 15 | ARFIP1 | 3'UTR | Deletion | 4 | 153832103 | T |
| 16 | ARL10 | 3'UTR | Deletion | 5 | 175800427 | T |
| 17 | BMPR2 | 3'UTR | Deletion | 2 | 203426177 | T |
| 18 | BTBD7 | 3'UTR | Deletion | 14 | 93708031 | A |
| 19 | C15orf2 | 3'UTR | Deletion | 15 | 24927892 | A |
| 20 | C17orf96 | 3'UTR | Deletion | 17 | 36829266 | T |
| 21 | CCDC89 | 3'UTR | Deletion | 11 | 85395560 | T |
| 22 | CCND1 | 3'UTR | Deletion | 11 | 69466274 | A |
| 23 | DIDO1 | 3'UTR | Deletion | 20 | 61536692 | A |
| 24 | EDEM1 | 3'UTR | Deletion | 3 | 5260541 | T |
| 25 | ENTPD4 | 3'UTR | Deletion | 8 | 23289681 | A |

TABLE 3-continued

Panel of 58 markers.

| Marker Nr. | Gene | Region | Type | Chromosome | Position | Reference base |
|---|---|---|---|---|---|---|
| 26 | FCHSD2 | 3'UTR | Deletion | 11 | 72548510 | A |
| 27 | FGFBP3 | 3'UTR | Deletion | 10 | 93666831 | A |
| 28 | FMO2 | 3'UTR | Deletion | 1 | 171178336 | A |
| 29 | FOXN2 | 3'UTR | Deletion | 2 | 48603080 | T |
| 30 | HDAC4 | 3'UTR | Deletion | 2 | 239974110 | A |
| 31 | HUS1B | 3'UTR | Deletion | 6 | 656080 | A |
| 32 | KDM5A | 3'UTR | Deletion | 12 | 393805 | T |
| 33 | KIF5C | 3'UTR | Deletion | 2 | 149879666 | T |
| 34 | LANCL1 | 3'UTR | Deletion | 2 | 211297866 | T |
| 35 | LRCH1 | 3'UTR | Deletion | 13 | 47325657 | A |
| 38 | MKLN1 | 3'UTR | Deletion | 7 | 131175981 | A |
| 37 | PCDHB3 | 3'UTR | Deletion | 5 | 140482944 | T |
| 38 | PPM1A | 3'UTR | Deletion | 14 | 60761434 | T |
| 39 | PURB | 3'UTR | Deletion | 7 | 44920831 | A |
| 40 | RYBP | 3'UTR | Deletion | 3 | 72424550 | T |
| 41 | RYR3 | 3'UTR | Deletion | 15 | 34157542 | A |
| 42 | SLC35F1 | 3'UTR | Deletion | 6 | 118638704 | A |
| 43 | ST7L | 3'UTR | Deletion | 1 | 113067471 | A |
| 44 | SULF2 | 3'UTR | Deletion | 20 | 46286321 | A |
| 45 | TMC7 | 3'UTR | Deletion | 16 | 19073948 | A |
| 46 | TMEM65 | 3'UTR | Deletion | 8 | 125325218 | A |
| 47 | TSR2 | 3'UTR | Deletion | X | 54471046 | T |
| 48 | UBA6 | 3'UTR | Deletion | 4 | 68481878 | T |
| 49 | UBE2Z | 3'UTR | Deletion | 17 | 47005702 | A |
| 50 | USP14 | 3'UTR | Deletion | 18 | 212030 | A |
| 51 | WHSC1L1 | 3'UTR | Deletion | 8 | 38175280 | A |
| 52 | ZNF185 | 3'UTR | Deletion | X | 152140996 | C |
| 53 | ZNF287 | 3'UTR | Deletion | 17 | 16454420 | T |
| 54 | CEPT1 | 5'UTR | Insertion/Deletion | 1 | 111690319 | A |
| 55 | ESCO1 | 5'UTR | Deletion | 18 | 19164371 | A |
| 56 | GRIA2 | 5'UTR | insertion/Deletion | 4 | 158142151 | A |
| 57 | SETBP1 | 5'UTR | insertion/Deletion | 18 | 42260910 | G |
| 58 | ZXDA | 5'UTR | Deletion | X | 57936947 | A |

Importantly, these markers can be used for determining MSI status independent of cancer type. Thus, in principle, diagnosing MSI status can be done with the markers provided herein for every type of cancer. However, since MSI is most often present in cancers with a deficiency in mismatch repair genes, it is particularly envisaged to diagnose MSI status in a tumor sample of tumors where MMR deficiency occurs more frequently than in other types. Accordingly, the cancer sample is typically a sample selected from a cancer of colorectal cancer, endometrial cancer, ovarian cancer, gastric cancer, leukemia, and a tumor of the Lynch syndrome.

Diagnosing MSI status typically implies drawing the conclusion of detecting the presence of MSI or not. The more marker genes presented in Tables 1-3 herein that have an indel in a microsatellite region, the higher the chance that the tumor is characterized by microsatellite instability.

Typically, MSI can be classified as MSI-H, MSI-L and MSS. According to particular embodiments, if 25% or more of the microsatellite regions used to diagnose MSI status contains an indel, the tumor is MSI-H, if between 2.5% and 25% of the microsatellite regions contains an indel, the tumor is MSI-L, and if less than 2.5% of the microsatellite regions contains an indel, the tumor is microsatellite stable. According to alternative embodiments, MSI can be classified as MSI-H if 20% or more of the microsatellite regions used to diagnose MSI status contains an indel; if between 2% (or 2.5%) and 20% of the microsatellite regions contains an indel, the tumor is MSI-L, and if less than 2% (or 2.5%) of the microsatellite regions contains an indel, the tumor is microsatellite stable. The latter classification is particularly preferred when a high number (e.g. 25 or more) of markers are used. Percentages are used rather than absolute numbers, as the number of markers can be varied by a skilled person. For instance, if 8 markers are used, the tumor will be MSS only if none of the microsatellite markers contains an indel; it will be MSI-H if 2 or more markers are positive, while it will be MSI-L if only one marker contains an indel. Since it is apparent from this example that one positive marker more or less can affect the diagnosis if a limited number of markers is used, it is particularly envisaged to use more markers. This is particularly helpful to reliably classify tumors as MSI-L. For instance, with the 2-20% classification, if the preferred marker panel of 58 markers is used, a tumor is MSS if 0 or 1 markers score positive, MSI-L if 2 to 11 markers score positive and MSI-H if 12 or more markers score positive.

Published work also suggests that MMR− tumors have a distinct response to standard treatments and emerging targeted therapies. Preclinical investigations suggest, for instance, that MMR-deficient tumors show resistance to 5-fluorouracil, anti-EGFR and VEGF therapies[25,26]. The precise reason for this heterogeneity is unknown, but presence or absence of secondary (recurrent) mutations as a consequence of MMR-deficiency might determine treatment outcome. For instance, we observed a recurrent mutation in KRAS, which acts as an established negative response predictor of anti-EGFR therapies. Interestingly, most recurrent mutations in endometrial tumors also specifically affect genes expressed in the normal endometrium and were differentially expressed in MMR− versus MMR+ tumors, suggesting positive clonal selection of these mutations. The identification of recurrent mutations also reveals several novel therapeutic targets for the treatment of MMR-deficient tumors.

Thus, according to some particular embodiments, the methods of diagnosing MSI status of a tumor, as presented herein, may further comprise a step of choosing the treatment regimen based on the MSI status (i.e. based on whether the tumor was found to be MSI-H, MSI-L or MSS).

The present methods all rely on the detection of indels in microsatellite regions of the genome. Frequently used methodologies for analysis of nucleic acid samples to detect indels will be briefly described. However, any method known in the art can be used in the invention to detect the presence of indels.

a. Allele-Specific Hybridization

This technique, also commonly referred to as allele specific oligonucleotide hybridization (ASO) (e.g., Stoneking et al., *Am. J. Hum. Genet.* 48:70-382, 1991; Saiki et al., *Nature* 324, 163-166, 1986; EP 235,726; and WO 89/11548), relies on distinguishing between two DNA molecules differing by one base by hybridizing an oligonucleotide probe that is specific for one of the variants to an amplified product obtained from amplifying the nucleic acid sample. This method typically employs short oligonucleotides, e.g. 15-20 bases in length. The probes are designed to differentially hybridize to one variant versus another. Principles and guidance for designing such probe is available in the art, e.g. in the references cited herein. Hybridization conditions should be sufficiently stringent that there is a significant difference in hybridization intensity between alleles, and producing an essentially binary response, whereby a probe hybridizes to only one of the alleles. Some probes are designed to hybridize to a segment of target DNA such that the polymorphic site aligns with a central position (e.g., in a 15-base oligonucleotide at the 7 position; in a 16-based oligonucleotide at either the 8 or 9 position) of the probe, but this design is not required.

The amount and/or presence of an allele is determined by measuring the amount of allele-specific oligonucleotide that is hybridized to the sample. Typically, the oligonucleotide is labeled with a label such as a fluorescent label. For example, an allele-specific oligonucleotide is applied to immobilized oligonucleotides representing sequences with different microsatellite length. After stringent hybridization and washing conditions, fluorescence intensity is measured for each microsatellite oligonucleotide.

Suitable assay formats for detecting hybrids formed between probes and target nucleic acid sequences in a sample are known in the art and include the immobilized target (dot-blot) format and immobilized probe (reverse dot-blot or line-blot) assay formats. Dot blot and reverse dot blot assay formats are described in U.S. Pat. Nos. 5,310,893; 5,451,512; 5,468,613; and 5,604,099; each incorporated herein by reference.

In a dot-blot format, amplified target DNA is immobilized on a solid support, such as a nylon membrane. The membrane-target complex is incubated with labeled probe under suitable hybridization conditions, unhybridized probe is removed by washing under suitably stringent conditions, and the membrane is monitored for the presence of bound probe.

In the reverse dot-blot (or line-blot) format, the probes are immobilized on a solid support, such as a nylon membrane or a microtiter plate. The target DNA is labeled, typically during amplification by the incorporation of labeled primers. One or both of the primers can be labeled. The membrane-probe complex is incubated with the labeled amplified target DNA under suitable hybridization conditions, unhybridized target DNA is removed by washing under suitably stringent conditions, and the membrane is monitored for the presence of bound target DNA. A reverse line-blot detection assay is described in the example.

b. Allele-Specific Primers

Indels can also be detected using allele-specific amplification or primer extension methods. These reactions typically involve use of primers that are designed to specifically target a polymorphism via a mismatch at the 3'-end of a primer. The presence of a mismatch effects the ability of a polymerase to extend a primer when the polymerase lacks error-correcting activity. For example, to detect an allele sequence using an allele-specific amplification- or extension-based method, a primer complementary to the normal allele of a microsatellite (i.e. without indel) is designed such that the 3'-terminal nucleotide hybridizes with the sequence containing the right number of repeats. The presence of the particular allele can be determined by the ability of the primer to initiate extension. If the 3'-terminus is mismatched, the extension is impeded.

In some embodiments, the primer is used in conjunction with a second primer in an amplification reaction. The second primer hybridizes at a site unrelated to the microsatellite. Amplification proceeds from the two primers leading to a detectable product signifying the particular allelic form is present. Allele-specific amplification- or extension-based methods are described in, for example, WO 93/22456; U.S. Pat. Nos. 5,137,806; 5,595,890; 5,639,611; and U.S. Pat. No. 4,851,331.

Using allele-specific amplification-based genotyping, identification of the alleles requires only detection of the presence or absence of amplified target sequences. Methods for the detection of amplified target sequences are well known in the art. For example, gel electrophoresis and probe hybridization assays described are often used to detect the presence of nucleic acids.

In an alternative probe-less method, the amplified nucleic acid is detected by monitoring the increase in the total amount of double-stranded DNA in the reaction mixture, is described, e.g. in U.S. Pat. No. 5,994,056; and European Patent Publication Nos. 487,218 and 512,334. The detection of double-stranded target DNA relies on the increased fluorescence various DNA-binding dyes, e.g., SYBR Green, exhibit when bound to double-stranded DNA.

As appreciated by one in the art, allele-specific amplification methods can be performed in reaction that employ multiple allele-specific primers to target particular alleles. Primers for such multiplex applications are generally labeled with distinguishable labels or are selected such that the amplification products produced from the alleles are distinguishable by size. Thus, for example, both alleles in a single sample can be identified using a single amplification by gel analysis of the amplification product.

As in the case of allele-specific probes, an allele-specific oligonucleotide primer may be exactly complementary to one of the polymorphic alleles in the hybridizing region or may have some mismatches at positions other than the 3'-terminus of the oligonucleotide, which mismatches occur at non-polymorphic sites in both allele sequences.

c. Detectable Probes i) 5'-Nuclease Assay Probes

Genotyping can also be performed using a "TaqMan®" or "5'-nuclease assay", as described in U.S. Pat. Nos. 5,210,015; 5,487,972; and 5,804,375; and Holland et al., 1988,

*Proc. Natl. Acad. Sci. USA* 88:7276-7280. In the TaqMan® assay, labeled detection probes that hybridize within the amplified region are added during the amplification reaction. The probes are modified so as to prevent the probes from acting as primers for DNA synthesis. The amplification is performed using a DNA polymerase having 5'- to 3'-exonuclease activity. During each synthesis step of the amplification, any probe which hybridizes to the target nucleic acid downstream from the primer being extended is degraded by the 5'- to 3'-exonuclease activity of the DNA polymerase. Thus, the synthesis of a new target strand also results in the degradation of a probe, and the accumulation of degradation product provides a measure of the synthesis of target sequences.

The hybridization probe can be an allele-specific probe that discriminates between the alleles with and without indels. Alternatively, the method can be performed using an allele-specific primer and a labeled probe that binds to amplified product.

Any method suitable for detecting degradation product can be used in a 5'-nuclease assay. Often, the detection probe is labeled with two fluorescent dyes, one of which is capable of quenching the fluorescence of the other dye. The dyes are attached to the probe, usually one attached to the 5'-terminus and the other is attached to an internal site, such that quenching occurs when the probe is in an unhybridized state and such that cleavage of the probe by the 5'- to 3'-exonuclease activity of the DNA polymerase occurs in between the two dyes. Amplification results in cleavage of the probe between the dyes with a concomitant elimination of quenching and an increase in the fluorescence observable from the initially quenched dye. The accumulation of degradation product is monitored by measuring the increase in reaction fluorescence. U.S. Pat. Nos. 5,491,063 and 5,571,673, both incorporated herein by reference, describe alternative methods for detecting the degradation of probe which occurs concomitant with amplification.

ii) Secondary Structure Probes

Probes detectable upon a secondary structural change are also suitable for detection of a polymorphism, including indels. Exemplified secondary structure or stem-loop structure probes include molecular beacons or Scorpion® primer/probes. Molecular beacon probes are single-stranded oligonucleic acid probes that can form a hairpin structure in which a fluorophore and a quencher are usually placed on the opposite ends of the oligonucleotide. At either end of the probe short complementary sequences allow for the formation of an intramolecular stem, which enables the fluorophore and the quencher to come into close proximity. The loop portion of the molecular beacon is complementary to a target nucleic acid of interest. Binding of this probe to its target nucleic acid of interest forms a hybrid that forces the stem apart. This causes a conformation change that moves the fluorophore and the quencher away from each other and leads to a more intense fluorescent signal. Molecular beacon probes are, however, highly sensitive to small sequence variation in the probe target (Tyagi S, and Kramer F. R., *Nature Biotechnology*, Vol. 14, pages 303-308 (1996); Tyagi et al., *Nature Biotechnology*, Vol. 16, pages 49-53 (1998); Piatek et al., *Nature Biotechnology*, Vol. 16, pages 359-363 (1998); Marras S. et al., *Genetic Analysis: Biomolecular Engineering*, Vol. 14, pages 151-156 (1999); Tpp I. et al, *BioTechniques*, Vol 28, pages 732-738 (2000)). A Scorpion® primer/probe comprises a stem-loop structure probe covalently linked to a primer.

d. DNA Sequencing and Single Base Extensions

Indels can also be detected by direct sequencing. Methods include e.g. dideoxy sequencing-based methods and other methods such as Maxam and Gilbert sequence (see, e.g. Sambrook et al., supra).

Other detection methods include Pyrosequencing™ of oligonucleotide-length products. Such methods often employ amplification techniques such as PCR. For example, in pyrosequencing, a sequencing primer is hybridized to a single stranded, PCR-amplified, DNA template; and incubated with the enzymes, DNA polymerase, ATP sulfurylase, luciferase and apyrase, and the substrates, adenosine 5' phosphosulfate (APS) and luciferin. The first of four deoxynucleotide triphosphates (dNTP) is added to the reaction. DNA polymerase catalyzes the incorporation of the deoxynucleotide triphosphate into the DNA strand, if it is complementary to the base in the template strand. Each incorporation event is accompanied by release of pyrophosphate (PPi) in a quantity equimolar to the amount of incorporated nucleotide. ATP sulfurylase quantitatively converts PPi to ATP in the presence of adenosine 5' phosphosulfate. This ATP drives the luciferase-mediated conversion of luciferin to oxyluciferin that generates visible light in amounts that are proportional to the amount of ATP. The light produced in the luciferase-catalyzed reaction is detected by a charge coupled device (CCD) camera and seen as a peak in a Pyrogram™. Each light signal is proportional to the number of nucleotides incorporated. Apyrase, a nucleotide degrading enzyme, continuously degrades unincorporated dNTPs and excess ATP. When degradation is complete, another dNTP is added.

Another similar method for characterizing indels does not require use of a complete PCR, but typically uses only the extension of a primer by a single, fluorescence-labeled dideoxyribonucleic acid molecule (ddNTP) that is complementary to the nucleotide to be investigated. The nucleotide at the polymorphic site can be identified via detection of a primer that has been extended by one base and is fluorescently labeled (e.g., Kobayashi et al, *Mol. Cell. Probes,* 9:175-182, 1995).

e. Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution (see, e.g. Erlich, ed., *PCR Technology, Principles and Applications for DNA Amplification*, W. H. Freeman and Co, New York, 1992, Chapter 7).

Distinguishing of microsatellite polymorphisms can be done using capillary electrophoresis. Capillary electrophoresis conveniently allows identification of the number of repeats in a particular microsatellite allele. The application of capillary electrophoresis to the analysis of DNA polymorphisms is well known to those in the art (see, for example, Szantai, et al, *J Chromatogr A*. (2005) 1079 (1-2):41-9; Bjorheim and Ekstrom, *Electrophoresis* (2005) 26(13):2520-30 and Mitchelson, *Mol Biotechnol*. (2003) 24(1):41-68).

f. Single-Strand Conformation Polymorphism Analysis

Alleles of target sequences can be differentiated using single-strand conformation polymorphism analysis, which identifies base differences by alteration in electrophoretic migration of single stranded PCR products, as described, e.g, in Orita et al., *Proc. Nat. Acad. Sci.* 86, 2766-2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence difference between alleles of target genes.

Indel detection methods often employ labeled oligonucleotides. Oligonucleotides can be labeled by incorporating a label detectable by spectroscopic, photochemical, biochemical, immunochemical, or chemical means. Useful labels include fluorescent dyes, radioactive labels, e.g. 32P, electron-dense reagents, enzyme, such as peroxidase or alkaline phosphatase, biotin, or haptens and proteins for which antisera or monoclonal antibodies are available. Labeling techniques are well known in the art (see, e.g. Sambrook et al., supra).

According to another aspect, a biomarker panel is provided for determining MSI in a tumor sample. Such biomarker panel comprises at least eight microsatellite regions selected from those present in 5' UTR or 3' UTR regions from the genes listed in Table 1 and those present in the exons of the genes listed in Table 2. According to very particular embodiments, the biomarker panel comprises at least half of the microsatellite regions listed in Table 3. According to yet even further particular embodiments, the biomarker panel are the 40 microsatellite regions listed in Table 3.

It is particularly envisaged that this biomarker panel can be used to detect MSI status in cancer. Accordingly, the use of this biomarker panel is provided in the diagnosis of microsatellite instability in cancer.

According to yet other embodiments, a kit is provided for determining MSI in a tumor sample, comprising the tools to genotype the biomarker panel (i.e. the at least eight microsatellite regions selected from those present in 5' UTR or 3' UTR regions from the genes listed in Table 1 and those present in the exons of the genes listed in Table 2). Most particularly, the kit will be adapted to the particularly envisaged biomarker panel(s).

It is to be understood that although particular embodiments, specific configurations as well as materials and/or molecules, have been discussed herein for cells and methods according to the present invention, various changes or modifications in form and detail may be made without departing from the scope and spirit of this invention. The following examples are provided to better illustrate particular embodiments, and they should not be considered limiting the application. The application is limited only by the claims.

EXAMPLES

Example 1. Whole-Genome Sequencing of an Endometrial Tumor with MMR-Deficiency

We sequenced the genomes from three primary endometrial tumors and their matched germ-line DNA samples using Complete Genomics® (CG) technology. Each of the tumor and normal genomes were sequenced with an average coverage of 95.2× and 77.1×, respectively. Remarkably, one of the tumors contained significantly more novel somatic mutations than the other tumors (104,124 versus 7,344 and 9,072 in the other tumors) using the verified CGAtools™ calldiff method (http://cgatools.sourceforge.net). This algorithm is designed to find differences between two genomes from the same individual, such as a tumor-normal pair). We therefore considered this tumor to exhibit a hypermutator phenotype. To exclude that the increased mutation load in the hypermutator was due to errors, 205 mutations were validated using standard Sequenom MassARRAY genotyping. Validation rates in the hypermutator and other tumors were at a comparable level (97.7% and 83.7%, respectively), indicating that most detected mutations were true variants. Overall, we thus observed that the mutation load in the hypermutator was 20.3-fold higher than in the other tumors (FIG. 1B), thereby confirming the 'mutator' phenotype of this tumor.

Human cancers characterized by MMR deficiency have been described in various cancer types, most commonly in endometrial and colorectal tumors. To assess the possibility that the hypermutator was caused by MMR-deficiency, standard diagnostic tests were performed, including immunohistochemistry of MMR genes[18] (MLH1, MSH2 and MSH6), assessment of microsatellite instability (MSI) using the extended Bethesda panel[9,17-15] and methylation profiling of the MLH1 promoter[19,20] (data not shown). In the hypermutator, we observed a positive MSI status and absence of MSH6 as determined by immunohistochemistry. Detailed inspection of somatic variants in the hypermutator sample indeed revealed a somatic frameshift insertion in exon 5 of MSH6 (rs63749866). No mutations were found in DNA polymerases or other known DNA repair genes, thereby confirming that the hypermutator phenotype was due to inactivation of MSH6.

Example 2. Somatic Mutation Patterns in the MSH6-Deficient Hypermutator

Figure 1:
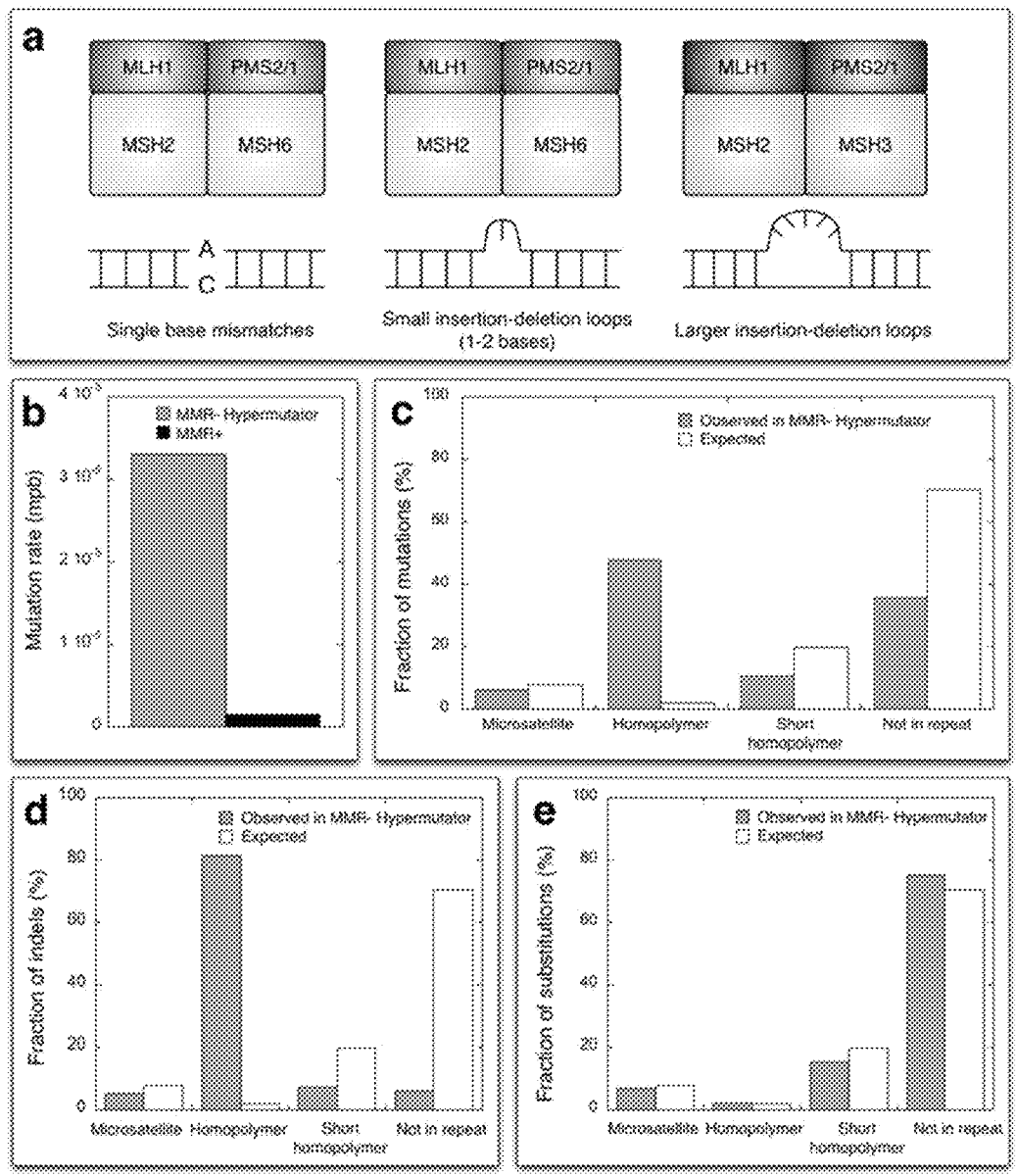
FIG. 1. Somatic substitutions and indels in a MMR-deficient hypermutator.

Knockout studies in model organisms and cell lines have indicated that somatic mutations arising due to MMR deficiency mainly affect DNA sequences consisting of short repeat units, in particular, microsatellites (here defined as mono- to hexanucleotide repeats with a minimal length of 6 bases and minimal two repeat units) and homopolymers (defined as mononucleotide repeats with n≥6). In our hypermutator, we observed that somatic mutations are more frequently located in homopolymers than expected based on their genome-wide occurrence (FIG. 1C).

Briefly, In order to test this hypothesis, we have stratified the genome into four different classes defined as follows:
Microsatellites with at least dinucleotide repeat: a di-, tri-, tetra, penta- or hexanucleotide repeat consisting of at least two repeat units and with a minimal length of 6 bases.
Homopolymer: a mononucleotide repeat with a minimal length of 6 bases.
Short homopolymer: a mononucleotide repeat of 3, 4 or 5 bases long.
Not in repeat: the remainder of the genome, i.e. every base that is not part of a simple repeat sequence The genomic regions following these definitions were determined by scanning the sequence files (in FASTA format) using the 'grepseq' tool (http://code.google.com/p/grepseq/) for the whole-genome. In the whole genome, the overall repeat composition was as follows: microsatellites (7.9%), homopolymers (1.9%), short homopolymers (19.8%), and lastly 70.4% not in a simple repeat region.

For all the somatic mutations in the hypermutator, we investigated how these somatic mutations accumulated in the four repeat regions described above. Somatic mutations in each repeat class were selected using the intersectBed command of BEDTools[21]. We observed that somatic mutations accumulate more frequently in homopolymers (47.7%) compared to their genome-wide occurrence (1.9%). 35.5%, 10.7% and 6.2% of the somatic mutations were located in non-repeat regions, short homopolymers and microsatellites, respectively. Compared to the genome-wide occurrence of these regions (i.e. 70.4%, 19.8% and 7.9% for non-repeat, short homopolymers and microsatellites, respectively), they were less frequently affected than expected (see also FIG. 1C).

Thus, non-repeat regions, short homopolymers (mononucleotide repeats with n=3 to 5 bases) and microsatellites of di- to hexanucleotide repeats were less frequently affected than expected. When stratifying somatic mutations for indels and single basepair substitutions, we noticed that indels were mainly confined to homopolymers (81.3%; FIG. 1D). On the other hand, substitutions predominantly affected non-repeat regions (75.1%; FIG. 1E). These data clearly indicate that indels arising due to MSH6-deficiency mainly occur in homopolymers and not microsatellites, whereas single basepair substitutions are confined to non-repeat regions.

Next, we evaluated whether somatic indels in the hypermutator follow a specific pattern. This analysis was limited to homopolymers, since the majority of indels was located in these sequences. Remarkably, A or T homopolymers were much more frequently affected (94.0%; FIG. 2A). However, since 92.2% of all homopolymers consist of A or T bases and are thus equally biased towards AT content, homopolymers consisting of C or G nucleotides were equally prone to accumulate indels. Genetic studies in lower organisms have suggested that the MSH6/MSH2 complex is involved in the recognition of insertion-deletions loops (IDLs) of one or two bases, which typically occur in homopolymers, whereas the MSH3/MSH2 complex is responsible for the recognition of longer IDLs, which are more often seen in microsatellites (FIG. 1A). We observed that up to 96.4% of indels consisted of one or two bases (FIG. 2B), thereby confirming that MSH6 is involved in the recognition of short IDLs. Previous studies have debated whether deletions occur more frequently than insertions; we observed that deletions were slightly less frequent than insertions (47.7% versus 52.3%; $P<10E-6$). For every somatic indel in the hypermutator, we also calculated the distance to the closest germ-line and somatic substitution and found that somatic substitutions were more often in the close proximity of an indel. Intriguingly, the substitution rate in the germ-line DNA of several eukaryotic organisms, including humans, is also elevated by nearby indel mutations. Finally, in contrast to previous studies showing that the probability of accumulating an indel increases with the length of the homopolymer, we observed a Gaussian distribution pattern, whereby homopolymers of length 11 were most frequently affected. It is possible, however, that indels affecting homopolymers with a length>11 are missed due to mapping errors of the gapped CG sequencing reads.

Example 3. Negative Clonal Selection in MMR-Deficient Exomes

Introduction

We also assessed whether somatic mutations in MMR-deficient tumors undergo positive or negative clonal selection. To this extent, we calculated mutation rates, which were defined as the number of observed mutations per base (mpb) in a given genomic region. For instance, 1 mutation observed in a region of $10^6$ bases would be listed as a mutation rate of 1E–06 mpb. In the hypermutator, we observed a genome-wide mutation rate of 3.3E–05 mutations per basepair (mpb) (FIG. 3A). Stratification of these mutation rates into exonic, intergenic and intronic regions revealed that the mutation rate in exons (excluding the 5' and 3' untranslated regions) was smaller than in intergenic or intronic regions (FIG. 3A). Additional stratification of mutation rates into substitutions and indels demonstrated that the substitution rate in the exome was decreased by 14.3% (FIG. 3B), whereas the decrease for indels was more pronounced, i.e., 74.7% (FIG. 3C). Correction of indel mutation rates relative to the number of homopolymers or the length of homopolymers in exonic, intergenic and intronic regions confirmed that the decrease in indels was not due to a lower number of homopolymers or due to shorter homopolymers in the exome. Intriguingly, the number of indels in non-repeat regions, short homopolymers and microsatellites was also decreased by 58.3%.

3.1. Mutation Rate of the Hypermutator in the Exome

We observed a genome-wide mutation rate of 3.3E–05 mpb. The mutation rate in the exome (i.e. exonic regions, excluding the 5' and 3' untranslated regions) was smaller than in intergenic or intronic regions. Stratification of mutation rates into substitutions and indels demonstrated that the substitution rate in the exome decreased by only 14.3% relative to the whole-genome, whereas the decrease for indels was more pronounced, i.e., 74.7%. Given that respectively 81.3% and 63.2% of indels were confined to homopolymers in the whole-genome and the exome, we investigated whether the decrease in indel rate in the exome could be explained by different characteristics of homopolymers in the whole-genome compared to the exome.

3.2. Correction of Indel Mutation Rates for Homopolymer Content

Firstly, the exome contains fewer homopolymers than the whole-genome (0.6% versus 1.9%), which might explain the decrease in indel rate in the exome. To test this hypothesis, we corrected the indel mutation rates by calculating the fraction of affected homopolymers (i.e. the number of affected homopolymers per homopolymer) present in a given region (under the assumption that one homopolymer would only contain one insertion or deletion). The corrected indel mutation rate in the exome was still much lower than in whole-genome, intergenic or intronic regions (as depicted in FIG. 4A), indicating that the decrease in indels is not due to a lower number of homopolymers in the exome.

Furthermore, we also corrected the indel mutation rate for the number of bases in homopolymers in the different genomic regions, which also takes the length of the homopolymer into consideration. As can be observed from FIG. 4B, the decrease in mutation rate for the exonic regions is still valid.

3.3. Correction of Indel Mutation Rates for Short Homopolymer Content

We observed that 78.8% of the exonic homopolymers have a length of 6, which is much higher than the proportion in the whole-genome (54.3%). Under the assumption that longer homopolymers have a higher chance to be affected than shorter homopolymers, as has been shown in previous studies, we wanted to investigate whether the decrease in indels was due to a higher proportion of short homopolymers in the exome. We stratified the affected homopolymers into two subgroups (i.e. homopolymer of length 6 and homopolymers with length>6). Then the mutation rate was defined as the number of affected homopolymers of a certain subgroup, divided by the number of homopolymer in given subgroup. This adjusted mutation rate was calculated for different regions. For homopolymers of length 6, a substantial decrease for the indel rate in the exome was observed (see FIG. 4C).

For homopolymers with a length larger than 6, we also noted a decrease in the indel rate in the exome compared to the whole-genome (1.14E−02 versus 1.19E−02), although the decrease was less pronounced than for the homopolymers of length 6. This indicates that the decreased indel rate in the homopolymer region in the exome cannot only be explained by a higher proportion of shorter homopolymers, although it clearly had an effect on the large overall decrease in indels.

3.4. Indel Mutation Rates in Non-Repeat Regions

In addition to the large proportion of indels affecting homopolymers, 18.7% and 36.8% of indels affected non-homopolymer regions in the whole-genome and the exome, respectively. The indel rate (defined as the number of indels divided by the total bases of non-homopolymer regions) for such indels was also calculated and revealed an obvious decrease for indels in exonic regions (not shown).

In summary, stratification of mutation rates into substitutions and indels, and additional stratification of mutation rates into indels affecting homopolymers and affecting non-homopolymer regions, revealed a reduction in the mutation rate in the exons, especially for indels. Indels located in exons cause frameshift mutations and are more likely to disrupt gene function than substitutions. These data therefore suggest that most indels result in reduced-fitness mutations that undergo negative clonal selection.

3.5. Effect on Indel Versus Substitution Mutation Rates in Exonic Regions

When we stratify the mutation rate into the substitution rate and the indel rate, and inspect the overall effect between the whole genome and the exome, we clearly observe a steeper drop in the indel rate than we do in the substitution rate (not shown). Since most indels consist of insertions or deletions of one or two bases, they will result in frameshift mutation in the exonic regions. The effect of a frameshift mutation on protein function is much more drastic than that of a single base substitution resulting in a (non-)synonymous, and it is therefore expected that indel mutations are under stronger negative selection than substitutions.

Example 4. Exome Sequencing of Mismatch Repair Deficient and Proficient Tumors and their Matched Normal Samples Next, we selected 11 other endometrial tumors, 7 of which were MMR-deficient (MMR−) based on absence of MLH1, MSH2 or MSH6 as determined by immunohistochemistry. All tumors were primary, chemo-naïve tumors. Tumor DNA was derived from fresh frozen tumor tissue, while matched normal DNA for these samples was extracted from peripheral white blood cells. DNA was extracted using the Qiagen DNAeasy kit for all samples. Detailed clinical information for all samples is listed in the table below.

| Tumor | Type | Histopathology | Grade | Stage |
|---|---|---|---|---|
| 1 MMR− 2 | Endometrium | Endometrioid carcinoma | 3 | IIIa |
| 2 MMR− 3 | Endometrium | Endometrioid carcinoma | 2 | Ib |
| 3 MMR− 4 | Endometrium | Endometrioid carcinoma | 3 | II |
| 4 MMR− 5 | Endometrium | Endometrioid carcinoma | 2 | Ia |
| 5 MMR− 6 | Endometrium | Serous carcinoma | 3 | Ib |
| 6 MMR− 7 | Endometrium | Endometrioid/ clear cell | 3 | Ia |
| 7 MMR− 8 | Endometrium | Serous/clear cell |  | Ib |
| 8 MMR+ 3 | Endometrium | Endometrioid carcinoma | 1 | IIIc |
| 9 MMR+ 4 | Endometrium | Serous carcinoma | 3 | IIIa |
| 10 MMR+ 5 | Endometrium | Mucinous carcinoma | 2 | IIIa |
| 11 MMR+ 6 | Endometrium | Endometrioid carcinoma | 1 | Ia |

4.1 Standard Diagnostics Tests

The table below describes the results of standard diagnostic tests in MSI determination (immunohistochemistry of MMR genes MLH1, MSH2 and MSH6; hypermethylation status of the MLH1 promoter regions; microsatellite instability using the extended Bethesda panel of 8 dinucleotide and 2 mononucleotide repeat markers) performed on the sequenced endometrial tumors. In the immunohistochemistry experiments, an asterisk (*) indicates weak positive nuclear staining in a minority of the tumor cells. Classification of MMR-deficiency status was performed using immunohistochemistry of the major MMR proteins (MLH1, MSH2 and MSH6). When either of these proteins were absent in the nucleus of tumor cells, the tumor was classified as MMR-deficient (MMR−), otherwise as MMR-proficient (MMR+).

| Tumor | IHC MLH1 | IHC MSH2 | IHC MSH6 | MSI (Bethesda) | MLH1 hyper-methylation |
|---|---|---|---|---|---|
| MMR− 2 | −(*) | + | − | + | + |
| MMR− 3 | − | + | + | + | + |
| MMR− 4 | + | − | − | − | +/− |
| MMR− 5 | + | − | − | + | − |
| MMR− 6 | + | + | − | + | − |
| MMR− 7 | − | − | − | − | − |
| MMR− 8 | + | − | − | − | − |
| MMR+ 3 | + | + | + | − | − |
| MMR+ 4 | + | + | + | − | − |
| MMR+ 5 | + | + | + | − | − |
| MMR+ 6 | + | + | + | − | − |

For the microsatellite instability test, detailed results for all markers included in the extended Bethesda panel are listed below.

| Tumor | BAT 25 | BAT 26 | D5S346 | D17S250 | D2S123 | TGFB | BAT 40 | B18S58 | D17S787 | D18S69 |
|---|---|---|---|---|---|---|---|---|---|---|
| MMR− 2 | + | + | + | N/A | N/A | N/A | − | N/A | − | + |
| MMR− 3 | − | + | − | + | + | + | − | + | − | − |
| MMR− 4 | − | − | − | − | − | − | N/A | − | − | − |
| MMR− 5 | + | − | + | + | + | + | N/A | − | − | − |
| MMR− 6 | + | − | + | + | + | − | + | − | − | + |
| MMR− 7 | − | − | − | − | − | − | − | − | − | − |
| MMR− 8 | − | − | − | − | − | − | − | − | − | − |
| MMR+ 3 | − | − | − | − | − | − | − | − | − | − |
| MMR+ 4 | − | − | − | − | − | − | − | − | − | − |
| MMR+ 5 | − | − | − | − | − | − | − | − | − | − |
| MMR+ 6 | − | − | − | − | − | − | − | − | − | − |

4.2 Sequencing, Mapping and Variant Calling for Exomes Sequenced with Illumina's HiSeq2000 Technology Exomes of the 11 endometrial tumor-normal pairs were captured using Illumina's TruSeq Exome Enrichment Kit (8 rxns). The TruSeq capture regions encompass 62 Mb, including 20,794 genes (201,121 exons). According to the RefGene definitions, 94.4%, 83.9% and 91.9% of the exonic regions, 5'UTR and 3'UTR are included in the targeted capture. Pre-enrichment DNA libraries were constructed according to the standard protocol from Illumina's TruSeq DNA Sample Preparation Guide. A 200- to 300-bp band was gel selected for each library and exome enrichment was performed according to Illumina's TruSeq Exome Enrichment Guide. Two rounds of biotinylated bait-based hybridizations were performed, followed by Streptavidin Magnetic Beads binding, a washing step and an elution step. A 10-cycle PCR enrichment was performed after the second elution and the enriched libraries were subjected to Illumina sequencing (HiSeq 2000). Libraries were denatured with sodium hydroxide and loaded onto an Illumina cBot for cluster generation according to the manufacturer's recommended protocols (TruSeq PE Cluster Kit v2.5). Lane 8 of the flow cell was reserved for a PhiX control. Paired-end sequencing (2×75 bp) was performed with TruSeq SBS kits. For each set of 6 indexed samples, 2 lanes were used.

Read Mapping and Alignment

BWA was used to align the raw reads from each sequencing lane (in fastq format) to the human reference genome (NCBI37/hg19) using default parameters. Aligned reads were processed and sorted with SAMtools (v.0.1.13) and PCR duplicates were removed with Picard MarkDuplicates (http://picard.sourceforge.net, v1.32). Base recalibration, local realignment around indels and single nucleotide variant calling were performed using the GenomeAnalysisTool-Kit (GATK v1.0.4487).

Variant Calling

Substitutions were called using the GATK Unified Genotyper[16], by using the settings specified below:

```
java -jar /path/to/GenomeAnalysisTK.jar \
    -R <reference_genome> \
    -T UnifiedGenotyper \
    -I <bamfile> \
    -o <output.vcf> \
    -stand_call_conf 30.0 \
    -stand_emit_conf 10 \
    --output_mode EMIT_ALL_SITES --all-bases
```

The most important settings are:
  stand_call_conf, which sets the minimum phred-scaled Qscore threshold to separate high confidence from low confidence calls. Only genotypes with a confidence 2 this threshold are emitted as called sites. 30 is the standard threshold for high-pass calling.
  stand_emit_conf. A threshold of 10 is recommended by GATK, which means that each variant with at least Q10 confidence to be non-reference is shown.
  all-bases: this setting enables output for each position in the genome, allowing to determine the coverage depth at each position for further filtering purposes.

The GATK Unified Genotyper produces a variant file in VCF format, which is explained in detail on the GATK wiki: http://www.broadinstitute.org/gsa/wiki/index.php/Understanding the Unified Genotyper%27s VCF files Small indels were detected using Dindel (v1.01) using the following script:

```
dindel --analysis getCIGARindels --bamFile <realigned_bam_file>
    --outputFile \
        <dindel_output> --ref <reference_genome>
makeWindows.py --inputVarFile <dindel_output.variants.txt>
    --windowFilePrefix <prefix> \
        --numWindowsPerFile 1000
dindel --analysis indels --doDiploid --bamFile
<realigned_dedup_bam_file> \
    --ref <reference_genome> --varFile <realign_var_file> \
    --libFile <dindel_output.libraries.txt> --outputFile
    <stage2_outputfiles>
mergeOutputDiploid.py --inputFiles <stage2_outputfiles>
--outputFile <IndelCalls.vcf> \
    --ref <reference_genome>
```

Similar to the somatic mutation detection presented for the whole-genomes in Note S1.4 (i.e the CGAtools calldiff method), a strategy to select reliable somatic variants was designed. List of somatic variants were generated by comparing the GATK variant files for the tumor and the matched normal (in VCF format). Somatic variants were defined as variants present in the tumor but not in the normal variant file. Initial quality filtering was performed based on the mapping quality score provided by the BWA mapper, which is reported in the GATK generated variant files for each base. A somatic mutation was retained only if the quality score was larger than Q30 for both the called base in the tumor sample and the matched normal sample. The table below does not only show the somatic mutations called in each of the endometrial exome samples, but also indicates what the effect of the Q30 filtering is on the proportion of the exome that is covered after filtering (i.e. what fraction of exonic bases is retained).

| Tumor | Exome covered in tumor (Q30) | Exome covered in normal (Q30) | Exome covered in inter-section (Q30) | Somatic substi-tutions | Somatic indels | Somatic muta-tions |
|---|---|---|---|---|---|---|
| MMR− 2 | 98.2% | 98.4% | 97.5% | 922 | 299 | 1,221 |
| MMR− 3 | 98.2% | 97.9% | 96.9% | 902 | 252 | 1,154 |
| MMR− 4 | 98.6% | 98.8% | 98.0% | 1,675 | 160 | 1,835 |
| MMR− 5 | 99.0% | 98.9% | 98.3% | 1,526 | 337 | 1,863 |
| MMR− 6 | 98.5% | 98.6% | 97.8% | 987 | 221 | 1,208 |
| MMR− 7 | 99.0% | 98.5% | 98.1% | 477 | 138 | 615 |
| MMR− 8 | 98.3% | 98.5% | 97.5% | 1,408 | 268 | 1,676 |
| MMR+ 3 | 98.3% | 98.4% | 97.6% | 327 | 73 | 400 |
| MMR+ 4 | 97.3% | 98.6% | 96.7% | 300 | 48 | 348 |
| MMR+ 5 | 98.0% | 97.6% | 96.7% | 384 | 78 | 462 |
| MMR+ 6 | 97.7% | 98.8% | 97.2% | 270 | 58 | 328 |

Further filtering was performed to select novel mutations only, using various data tracks, which were then applied to the variant lists using the intersectBed command of BED-Tools[21].

| | After quality filtering | | | After removing common variants | | |
|---|---|---|---|---|---|---|
| Tumor | Somatic substi-tutions | Somatic indels | Somatic muta-tions | Somatic substi-tutions | Somatic indels | Somatic muta-tions |
| MMR− 2 | 922 | 299 | 1,221 | 778 | 295 | 1,073 |
| MMR− 3 | 902 | 252 | 1,154 | 655 | 249 | 904 |
| MMR− 4 | 1,675 | 160 | 1,835 | 1,476 | 156 | 1,632 |

-continued

|  | After quality filtering | | | After removing common variants | | |
| --- | --- | --- | --- | --- | --- | --- |
| Tumor | Somatic substitutions | Somatic indels | Somatic mutations | Somatic substitutions | Somatic indels | Somatic mutations |
| MMR− 5 | 1,526 | 337 | 1,863 | 1,304 | 335 | 1,639 |
| MMR− 6 | 987 | 221 | 1,208 | 792 | 217 | 1,009 |
| MMR− 7 | 477 | 138 | 615 | 283 | 135 | 418 |
| MMR− 8 | 1,408 | 268 | 1,676 | 1,196 | 261 | 1,457 |
| MMR+ 3 | 327 | 73 | 400 | 22 | 2 | 24 |
| MMR+ 4 | 300 | 48 | 348 | 41 | 2 | 43 |
| MMR+ 5 | 384 | 78 | 462 | 46 | 2 | 48 |
| MMR+ 6 | 270 | 58 | 328 | 35 | 5 | 40 |

Validation of Somatic Substitutions and Indels Using Sequenom MassARRAY 107 novel somatic substitutions and 69 novel somatic indels were randomly selected from two randomly chosen MMR− samples for validation using Sequenom MassARRAY genotyping. The validation rate was 86.9% and 87.0% for substitutions and indels respectively. All somatic substitutions and indels in MMR+ tumors (531 in total), including nonsynonymous and synonymous substitutions as well as frameshift indels, were validated using Sequenom MassARRAY genotyping. Validation rates and the number of novel somatic mutations are shown in the tables below. As for the whole-genome sequencing validation studies, we observed a high validation rate in the MMR− hypermutator samples, while the indels in MMR+ tumors revealed low validation rates. The high confidence of both substitutions and indels in the MMR− tumors ensures that the patterns derived from these samples are not skewed by false positive predictions.

|  | Somatic substitutions | | | Somatic indels | | |
| --- | --- | --- | --- | --- | --- | --- |
| Tumor | Confirmed | Not confirmed | Validation rate | Confirmed | Not confirmed | Validation rate |
| MMR− 2 | 42 | 10 | 80.8% | 39 | 6 | 86.7% |
| MMR− 4 | 51 | 4 | 92.7% | 21 | 3 | 87.5% |
| MMR+ 3 | 22 | 75 | 22.7% | 2 | 25 | 7.4% |
| MMR+ 4 | 41 | 70 | 36.9% | 2 | 18 | 10.0% |
| MMR+ 5 | 46 | 73 | 38.7% | 2 | 33 | 5.7% |
| MMR+ 6 | 35 | 65 | 35.0% | 4 | 18 | 18.2% |

For the MMR-deficient tumors, the overall validation rate is high (87%), albeit lower than in the whole-genome mutation data. This can largely be attributed to a lower overall coverage depth in the exome sequencing data compared to the whole-genome sequencing data. However, since the observed patterns in MMR− tumors in the whole-genome and exome are largely congruent, we have accepted the 10% overestimation of somatic mutations in the MMR− exomes.

Overall mutation data after filtering and validation rounds are listed in the table below:

|  | After quality filtering | | | After removing common variants | | | After validation | | |
| --- | --- | --- | --- | --- | --- | --- | --- | --- | --- |
| Tumor | Somatic substitutions | Somatic indels | Somatic mutations | Somatic substitutions | Somatic indels | Somatic mutations | Somatic substitutions | Somatic indels | Somatic mutations |
| MMR− 2 | 922 | 299 | 1,221 | 778 | 295 | 1,073 | 778 | 295 | 1,073 |
| MMR− 3 | 902 | 252 | 1,154 | 655 | 249 | 904 | 655 | 249 | 904 |
| MMR− 4 | 1,675 | 160 | 1,835 | 1,476 | 156 | 1,632 | 1,476 | 156 | 1,632 |
| MMR− 5 | 1,526 | 337 | 1,863 | 1,304 | 335 | 1,639 | 1,304 | 335 | 1,639 |
| MMR− 6 | 987 | 221 | 1,208 | 792 | 217 | 1,009 | 792 | 217 | 1,009 |
| MMR− 7 | 477 | 138 | 615 | 283 | 135 | 418 | 283 | 135 | 418 |
| MMR− 8 | 1,408 | 268 | 1,676 | 1,196 | 261 | 1,457 | 1,196 | 261 | 1,457 |
| MMR+ 3 | 327 | 73 | 400 | 160 | 71 | 231 | 22 | 2 | 24 |
| MMR+ 4 | 300 | 48 | 348 | 169 | 45 | 214 | 41 | 7 | 43 |
| MMR+ 5 | 384 | 78 | 462 | 172 | 73 | 245 | 46 | 2 | 48 |
| MMR+ 6 | 270 | 58 | 328 | 149 | 54 | 203 | 35 | 5 | 40 |

Somatic Mutation Patterns for MMR− Exomes

For the substitutions and indels in the 7 MMR− exomes, a similar analysis as described in Example 3 was performed. As shown in FIG. 5A, in the 7 MMR− tumors, indels (shown in blue) were mainly confined to homopolymers (47.2%) and less frequently affected microsatellites, short homopolymers and non-repeat regions than expected based on the repeat composition of the exome (shown in red).

On the other hand, as shown in FIG. 5B, substitutions (shown in blue) were overrepresented in non-repeat regions (81.5%), but not in (short) homopolymers or microsatellites, comparable to the repeat composition of the exome (shown in red). These distributions confirmed our observations in the hypermutator whole-genome.

Stratification of Pattern Analyses for MLH1- and MSH2-Deficiency

Since several MMR− tumors were also deficient for MLH1 or MSH2, we assessed whether somatic mutation patterns differed depending on MLH1- or MSH2-deficiency. We studied 3 MMR− tumors with MLH1-deficiency versus 5 MMR− tumors without MLH1-deficiency, as well as 4 MMR− tumors with MSH2-deficiency versus 4 MMR− tumors without MSH2 deficiency.

The substitution rates and indel rates for MLH1-deficient tumors were 1.8E−05 and 7.1E−06 respectively, while for MLH1-proficient tumors they were 3.2E−05 and 7.1E−06 respectively. A bias towards single basepair transitions was observed in both MLH1-deficient tumors and MLH1-proficient tumors with A:G>G:C and G:C>A:T transitions representing up to 81.2% and 72.2% of all somatic substitutions respectively. Substitutions were both confined to non-repeat regions for MLH1-deficient tumors and MLH1-proficient tumors (80.3% and 81.5% respectively), whereas somatic indels were more prevalent in homopolymers (46.8% and 50.4% respectively). The fractions of somatic substitutions and indels in the different repeat categories in MLH1-deficient (shown in blue) and MLH1-proficient (shown in red) tumors are shown in FIG. 6.

Analogous analyses were performed on MSH2-deficient and MSH2-proficient tumors, where we observed that the substitution rates and indel rates for MSH2-deficient tumors were 2.1E−05 and 7.2E−06 respectively, while for MSH2-proficient tumors they were 3.3E−05 and 6.9E−06 respectively. A similar bias towards single basepair transitions was also observed in both MSH2-deficient tumors and MSH2-proficient tumors with A:G>G:C and G:C>A:T transitions representing up to 80.6% and 76.3% of all somatic substitutions respectively. Substitutions were both confined to non-repeat regions for MSH2-deficient tumors and MSH2-proficient tumors (80.8% and 81.5% respectively), whereas somatic indels were more prevalent in homopolymers (43.0% and 54.9% respectively). The fractions of somatic substitutions and indels in microsatellites, homopolymers, short homopolymers and non-repeat regions in MSH2-deficient (shown in blue) and MSH2-proficient (shown in red) tumors are shown in FIG. 7.

Comparing the distributions of somatic indels in different repeat categories with the distribution of MSH6-deficient hypermutator, both for MLH1-deficient tumors and for MSH2-deficient tumors, revealed that although indels were indeed more common in microsatellites (13.3% and 12.6% versus 5.4% in the MSH6-deficient hypermutator), homopolymers were still more frequently affected (46.8% and 43.0% in MLH1- and MSH2-deficient tumors versus 81.3% in the hypermutator).

CONCLUSION

Exome sequencing of these tumors and matched germline DNAs using Illumina technology revealed that there were 8,132 somatic events in MMR− tumors versus 893 in the MMR-proficient (MMR+) tumors. Validation of 176 somatic events in MMR− tumors showed that most mutations were true somatic events (86.9%). Since the validation rate in MMR+ tumors was much lower, all mutations in MMR+ tumors were validated. After validation, the number of mutations in MMR− tumors was 30-fold increased relative to MMR+ tumors (FIG. 8A). Remarkably, 79.7% of all mutations in MMR− tumors represented substitutions, resulting in mutation rates of 2.9E−05 and 7.3E−06 mbp for substitutions and indels, respectively (FIG. 8B). The fact that substitutions were more frequent than indels and that mutation rates were similar to those observed in the hypermutator exome, confirms that exonic mutations in MMR− tumors are subject to negative clonal selection. Similar to the MSH6-deficient hypermutator genome, transitions represented 79.2% of the substitutions in MMR− tumors. Substitutions were also confined to non-repeat regions (81.5%), whereas somatic indels were more prevalent in homopolymers (47.2%). Since several of these tumors were deficient for MLH1 or MSH2, we also stratified mutation patterns according to MLH1- or MSH2-deficiency and assessed whether microsatellites in MLH1- or MSH2-deficient tumors were affected by indels. Although indels were indeed more common in microsatellites (13.3% and 12.6% versus 5.4% in the MSH6-deficient hypermutator), homopolymers were still more frequently affected (46.8% and 43.0% in MLH1- and MSH2-deficient tumors versus 81.3% in the hypermutator; FIG. 8C-D).

Example 5. Positive Clonal Selection and Recurrent Mutations in MMR-Deficient Tumors 5.1 Analysis of Recurrently Affected Homopolymers Whereas the mutation rate in the exomes of MMR− tumors revealed evidence of negative selection, some mutations may also stimulate carcinogenesis. Such mutations could contribute to clonal expansion of the tumor and are expected to recurrently affect MMR− tumors. Since indels in homopolymers are more likely to affect gene function, we first screened all 30,111 exonic homopolymers in each of the 8 MMR− tumors of Example 4; 746 (2.5%) homopolymers were affected at least once versus 90 (0.3%) homopolymers in at least two tumors. Remarkably, 22 and 4 homopolymers were affected in 3 or 4 tumors, whereas 3 and 2 homopolymers were even affected in 5 or 6 tumors (Table 2). Out of the 31 homopolymers affected in 3 out of 8 tumors, 11, 15 and 5 consisted of A, T or C stretches, respectively.

For the 90 homopolymers affected in 2 out of 8 tumors, respectively 35, 32, 12 and 11 consisted of A, T, G or C stretches. The length of recurrently affected homopolymers varied from 7 nucleotides to 12 nucleotides. However, a strong bias towards homopolymers with length 8-11 nucleotides affected 3 out of 8 times was observed from FIG. 9A.

For the homopolymers affected in 2 out of 8 tumors, homopolymers with length between 6 and 25 were affected, strongly biased for lengths between 7 and 11 (FIG. 9B).

In fact, none of the 90 recurrently affected homopolymers or 40 recurrent substitutions were also present in MMR-proficient tumors. However, some of the genes were affected in both MMR-proficient and deficient tumors, albeit at different genomic locations.

5.2 Expected Versus Observed Frequency of Recurrent Indels

To assess whether recurrent indels are a consequence of positive selection and not a mere consequence of the increased indel rate in hypermutators, we calculated the expected frequency of recurrent indels. First, we calculated the overall expected frequency of indels in homopolymers in the whole-genome hypermutator sample, as in the whole genome we did not expect any bias due to positive or negative selection. Since indel errors due to slippage during replication are expected to increase with homopolymer length, we calculated the expected frequency ($f_{e,genome}$) separately for homopolymer lengths between 6 and 11 bases, as these represent the majority of exonic homopolymers (95.4%, Note S5).

| Length of homopolymer | Number of affected homopolymers | Total number of homopolymers (whole-genome) | Observed frequency in whole-genome ($f_{e,\,genome}$) |
|---|---|---|---|
| 6  | 4,868 | 4,123,709 | 1.18E−03 |
| 7  | 7,332 | 1,583,507 | 4.63E−03 |
| 8  | 8,729 | 562,325   | 1.55E−02 |
| 9  | 8,100 | 319,266   | 2.54E−02 |
| 10 | 5,861 | 206,595   | 2.84E−02 |
| 11 | 4,602 | 126,018   | 3.65E−02 |

For the 8 MMR deficient tumors, we can calculate the observed frequency ($f_{o,exome}$) of a homopolymer to be affected using the average number of affected homopolymers for each length. The fold-enrichment is then calculated as the ratio of the observed and expected frequencies.

| Length of homopolymer | Average number of affected homopolymers | Total number of homopolymers (exome) | Observed frequency in exome ($f_{o,\,exome}$) | Fold enrichment |
|---|---|---|---|---|
| 6  | 28.5 | 24,008 | 1.19E−03 | 1.0 |
| 7  | 33.6 | 4,787  | 7.02E−03 | 1.5 |
| 8  | 25.8 | 938    | 2.75E−02 | 1.8 |
| 9  | 10.8 | 205    | 5.24E−02 | 2.1 |
| 10 | 6.5  | 60     | 1.08E−01 | 3.8 |
| 11 | 4.1  | 24     | 1.72E−01 | 4.7 |

Assuming that every homopolymer of the same length has an equally high chance of being affected, the probability of homopolymers being affected in two or three independent tumors can be calculated as the product of the probability of a homopolymer being affected in one tumor (i.e. the observed genome-wide frequency $f_{genome}$).

As such, the expected frequency of a homopolymer being affected in two tumors was calculated as follows:

$$f_{e,recurrent\ in\ 2} = (f_{e,genome})^2$$

and for an Indel to be Affected in Three Tumors:

$$f_{e,recurrent\ in\ 3} = (f_{e,genome})^3$$

To calculate the expected number of recurrent indels in two, respectively three tumors we multiplied the expected frequencies with the number of homopolymers in the exome, and with the number of ways we can draw 2, resp. 3, samples out of 8 samples (i.e. the number of combinations C(2,8) and C(3,8)). Thus, the number of expected recurrent indels in 8 tumors is calculated as follows:

$$N_{recurrent\ in\ 2} = C(2,8) * N_{homopolymers} * f_{e,recurrent\ in\ 2}$$

$$N_{recurrent\ in\ 3} = C(3,8) * N_{homopolymers} * f_{e,recurrent\ in\ 3}$$

For indels recurring in two tumors, the data are as follows:

| Length of homopolymer | Observed number of recurrent indels | Expected number of recurrent indels | Fold increase |
|---|---|---|---|
| 6  | 3  | 0.9 | 1.6 |
| 7  | 17 | 2.9 | 3.0 |
| 8  | 25 | 6.3 | 2.0 |
| 9  | 15 | 3.7 | 2.0 |
| 10 | 16 | 1.4 | 5.9 |
| 11 | 12 | 0.9 | 6.7 |

Although we already see an enrichment of indels recurring in two samples, the enrichment of indels recurring in three or more samples is much stronger:

| Length of homopolymer | Observed number of recurrent indels | Expected number of recurrent indels | Fold increase |
|---|---|---|---|
| 6  | 0 | 1.11E−03 | 0.0  |
| 7  | 2 | 1.33E−02 | 75.2 |
| 8  | 8 | 9.82E−02 | 40.7 |
| 9  | 7 | 9.37E−02 | 37.3 |
| 10 | 7 | 3.84E−02 | 91.2 |
| 11 | 6 | 3.27E−02 | 91.7 |

In summary, although the majority of homopolymers in the exome consist of 6 nucleotides, most recurrently affected homopolymers exhibited a length of 8-11 nucleotides. We therefore assessed the possibility that these homopolymers were recurrently affected due to their increased length. We calculated the genome-wide probability that a homopolymer of a specific length was affected by an indel in the hypermutator and found that the number of observed mutations in the exome was higher than expected for every homopolymer length. We also calculated the genome-wide probability to observe recurrent indels in homopolymers of a specific length and found that the observed number of exonic recurrent mutations in >2 or >3 tumors was much higher than expected for each homopolymer length, thus indicating that exonic homopolymers were not recurrently affected due to increased length. This indicates that these indels in these homopolymers are positively selected in these cancers.

Example 6. Recurrent Indels in 3' and 5'UTRs Affect Long Homopolymers

Since 5' and 3'UTRs of genes are also involved in regulating gene expression, we assessed whether somatic mutations in these regions underwent clonal selection. We used exome data of MMR-tumors, in which 83.9% and 91.9% of the 5' and 3'UTR regions were reliably sequenced.

6.1 Recurrent Indels in Regulatory Regions

To assess whether any of 5'UTR and 3'UTR regions were affected by recurrent mutations, we screened 5,367 and 59,259 homopolymers located in the exome-captured 5'UTRs and 3'UTRs of 7 MMR-deficient tumors, respectively. These homopolymers were also screened in the 5'UTRs and 3'UTRs of the whole-genome sequenced hypermutator sample.

Recurrent indels in homopolymers were much more frequent than expected from the observations in the exome: in the 3'UTR regions we observed 596 indels recurring in at least 3 out of 8 tumors and 1,215 in at least 2 out of 8 tumors, while in the 5'UTR we observed 30 indels recurring in at least 3 out of 8 tumors and 58 in at least 2 out of 8. In contrast, recurrent substitutions were very rare: in 3'UTR regions, 5 recurrent substitutions were found in at least 3 out of 8 tumors, and 25 in at least 2 out of 8 tumors; while in the 5'UTR regions 5 recurrent substitutions were observed in two samples, and no substitution was encountered in 3 or more samples. A list of the most recurrent indels in homopolymers in 5'UTR (present in at least 3 out of 8 tumors) and 3'UTR regions (present in at least 6 out of 8 tumors) in MMR deficient tumors is shown in Table 1.

6.1.1. Homopolymer Length and Recurrence of Somatic Mutation in Exonic Regions. 5'UTRs and 3'UTRs We wanted to investigate whether the length of homopolymers determines recurrence in exons, 5'UTRs and 3'UTRs. By screening the reference genome, we observed homopolymers in 5'UTRs and 3'UTRs are longer than in the exome. For instance, the exome contains 29,733 (98.8%) homopolymers of length<9 nucleotides while 5'UTRs and 3'UTRs contain 4,857 (90.5%) and 49,769 (84.0%) such homopolymers respectively. The exact number of homopolymers stratified for length in the exome (shown in blue), 5'UTRs (shown in red) and 3'UTRs (shown in green) are shown in FIG. 10A.

Although the absolute number of shorter homopolymers (length 6) in the 3'UTR is comparable to that of the exome (see figure above), the absolute number of affected homopolymers does not show the same pattern as the exome data (FIG. 10B).

In particular, a much higher number of homopolymers was affected in the 3'UTR than in the exonic and 5'UTR regions.

When looking into the recurrently affected homopolymers shorter than 9 nucleotides in the exome, in 5' and 3'UTRs respectively, we observed that a higher fraction of homopolymers shorter than 9 were affected in the exome compared to the 5' and 3' UTR. Only 1 out of 30 (3.3%) and 6 out of 596 (1.0%) were in 5' and 3'UTRs, respectively, while at least 10 out of 31 (32.3%) were found in the exome.

In absolute numbers, we again observe that a much higher number of homopolymers is recurrently affected in the 3'UTR (FIG. 10C).

To avoid bias due to a higher number of homopolymers shorter than 9 in the exome, the fraction of affected homopolymers with length<9 was corrected for the number of such homopolymers was performed in the three regions as follows:

$$\text{Corrected fraction} = \frac{\text{Fraction}}{\left(\frac{\text{Number of homopolymer with length} < 9 \text{ in a given region}}{\text{Average number of homopolymer with length} < 9 \text{ in three regions}}\right)}$$

After correction, the enrichment for shorter recurrent homopolymers in the exome was still observed (30.8% with length<9) compared to in 5' (19.0%) and 3'UTRs (0.6%). These data clearly indicate that homopolymer length critically determines which homopolymers are recurrently affected in 5' and 3'UTR regions, whereas in the exome, homopolymer length as well as the effect of the mutation on clonal growth advantage determine which homopolymers are recurrently affected. The table below shows an overview of the data described in the previous paragraphs.

|  | Exome | 5'UTRs | 3'UTRs |
|---|---|---|---|
| Number of recurrently affected homopolymer | 31 | 30 | 596 |
| Number of recurrently affected homopolymer with length <9 | 10 | 1 | 6 |
| Percentage of recurrently affected homopolymer with length <9 | 32.3% | 3.3% | 1.0% |
| Number of homopolymers with length <9 | 29,377 | 4,857 | 49,769 |
| Percentage of recurrently affected homopolymer with length <9 correcting for the number of homopolymers with length <9 | 30.8% | 19.0% | 0.6% |

Thus, in summary, homopolymers in 5' and 3'UTRs were longer than in the exome. For instance, 9.5% and 16.0% of the sequenced homopolymers in 5' and 3'UTRs consisted of >8 nucleotides versus only 1.3% in the exome (FIG. 11A). In contrast to the hypermutator, the probability of accumulating indels in homopolymers did not decrease for homopolymers of >11 nucleotides, but increased up to a length of 14 nucleotides and then remained constant for homopolymers of >14 nucleotides (FIG. 11B) This was most likely due to a difference in sequencing technology (Complete Genomics for the hypermutator whole-genome versus Illumina for exome sequencing). Consequently, since homopolymers in 5' and 3'UTRs are longer, the indel rate in these regions was considerably higher than in the exome (3.8 and 10.7-fold increased relative to the exome; FIG. 11C). However, only 1 out of 44 (2.3%) and 5 out of 1,058 (0.5%) recurrently affected homopolymers in 5' and 3' UTRs were <9 nucleotides in length. In contrast, in the exome, at least 10 out of 32 (31.3%) recurrent indels had a homopolymer length<9 (FIG. 11D). This difference was not due to a higher number of homopolymers with length<9 in the exome. Combined with our previous observations, these data therefore indicate that homopolymer length more critically determines which homopolymers are recurrently affected in 5' and 3'UTR regions, whereas in the exome, the effect of the mutation on clonal growth advantage, perhaps in combination with homopolymer length, determines which homopolymers are recurrently affected.

Example 7. Gene Expression Profiles of Recurrently Mutated Genes

Since we have hypothesized that recurrent mutations are linked with positive selection due to growth advantage for the tumor, the genes affected by these recurrent mutations should at least be expressed in normal endometrial tissue, and it is also expected that at least a subset of these genes may be found in other mismatch repair deficient tumors. Therefore, we analysed the expression profiles of genes affected by recurrent mutations both in the context of endometrium-specific expression and in the context of genes differentially expressed in colorectal MMR-deficient tumors.

7.1 Gene Expression in Normal Endometrium

Expression data for genes in normal endometrium tissue were downloaded from the Gene Expression Atlas[23] (http://www.ebi.ac.uk/gxa/) using the query "all genes over/under/non-differentially expressed in Homo sapiens, endometrium". This query resulted in 14,664 genes, of which 9,021 were overexpressed in the normal endometrium, 463 were underexpressed, and 5,180 showed no differential expression. Since the over- and underexpression was calculated with respect to general gene expression profiles throughout different tissue types, it is difficult to assess whether underexpressed genes are effectively absent (not expressed) or merely expressed at a lower level. However, for genes significantly overexpressed in endometrial tissue we can safely argue that they at least play a role within the normal endometrium. Therefore, in this analysis we have limited ourselves to genes overexpressed in normal endometrium.

Mutations from different datasets were compared with the derived expression data: all genes mutated in MMR-proficient tumors (MMR+ genes), all genes mutated in MMR-deficient tumors (MMR− genes), all genes recurrently affected in MMR-deficient tumors (defined as 3 out of 8 samples, Recurrent Genes), all recurrent indels in 3'UTR and 5'UTR regions (Recurrent 3'UTR and 5'UTR) and finally all recurrent indels in exonic regions (Recurrent Exonic). This analysis indicated that the recurrent mutations were overrepresented in genes that were overexpressed in normal endometrium tissue. Full data for these analyses are shown in the table below.

|  | Dataset | MMR+ genes | MMR– Genes | Recurrent Genes | Recurrent 3'UTR | Recurrent 5'UTR | Recurrent Exonic |
|---|---|---|---|---|---|---|---|
| Affected genes | 14,664 | 380 | 3,732 | 358 | 548 | 29 | 30 |
| Genes in dataset | 14,664 | 243 | 2,704 | 259 | 462 | 25 | 22 |
| Overexpressed | 9,021 | 141 | 1,732 | 180 | 349 | 18 | 20 |
|  |  | (58.0%) | (64.1%) | (69.5%) | (75.5%) | (72.0%) | (90.9%) |
| Underexpressed | 463 | 4 | 101 | 15 | 24 | 0 | 0 |
|  |  | (1.7%) | (3.7%) | (5.8%) | (5.2%) | (0%) | (0%) |
| Non-differentially expressed | 5,180 | 98 | 871 | 64 | 89 | 7 | 2 |
|  |  | (40.3%) | (32.2%) | (24.7%) | (19.3%) | (28.0%) | (9.1%) |

Analysis in Genes Specific for Microsatellite Instable Colorectal Cancers

Genes differentially expressed between microsatellite instable (MSI-H) and microsatellite stable (MSS) colorectal cancers were derived from a study by Banerjea et al[22]. In this study, 133 colorectal tumours were analysed of which 29 (22%) tumours were identified as MSI-H. Gene expression data were derived from Affymetrix HG-U133A chips. The derived dataset contains 4,874 genes differentially expressed between microsatellite instable and stable cancers (P<0.05, Benjamini and Hochberg False Discovery Rate).

Mutations from different datasets were compared with the derived expression data: all genes mutated in MMR-proficient tumors (MMR+ genes), all genes mutated in MMR-deficient tumors (MMR– genes), all genes recurrently affected in MMR-deficient tumors (defined as 3 out of 8 samples, Recurrent Genes), all recurrent indels in 3'UTR and 5'UTR regions (Recurrent 3'UTR and 5'UTR) and finally all recurrent indels in exonic regions (Recurrent Exonic).

| Data set | MMR+ Genes | MMR– Genes | Recurrent Genes | Recurrent 3'UTR | Recurrent 5'UTR | Recurrent Exonic |
|---|---|---|---|---|---|---|
| 4874 | 330 | 3,732 | 358 | 548 | 29 | 29 |
| Differentially expressed in MSI-H | 63 (16.6%) | 799 (21.4%) | 37 (24.3%) | 169 (30.3%) | 10 (34.5%) | 9 (31.0%) |

SUMMARY

To assess whether recurrent mutations influence gene expression, we used publicly available expression data from the Gene Expression Atlas[23] and assessed whether genes affected by recurrent indels or substitutions, are expressed in normal endometrium tissue. Of all genes that were mutated in MMR+ and MMR– tumors, respectively 63% and 64% were expressed in normal endometrium tissue. On the other hand, 71%, 75% and even 91% of genes with recurrent mutations in 5'UTR, 3'UTR and exonic regions were expressed. This clearly illustrates that recurrent mutations in exons, and to a much lesser extent also those located in 5' and 3'UTRs, specifically affect genes that are expressed in the endometrium. Furthermore, when comparing the set of recurrently affected genes to gene expression signatures specific for MMR– tumors (i.e., colorectal MMR– versus MMR+ tumors[22]), a significant increase in the proportion of genes differentially expressed in MSI tumors was noticed (see table above). In particular, 19% and 21% of the affected genes in MMR+ and MMR– tumors was differentially expressed compared to 46%, 31% and 35% of the genes with recurrent mutations in 5'UTR, 3'UTR and exonic regions. Most recurrent mutations thus also alter expression of genes, in which they are located, thereby further confirming that recurrent mutations, especially those located in the exome, are under positive clonal selection and could act as driver mutations of MMR– tumors.

Example 8. Recurrent Mutations as a Diagnostic Panel of MSI in Various Tumor Types The extended Bethesda panel, which consists of 8 microsatellite markers and 2 homopolymer markers is currently used to diagnostically assess MSI as a marker of MMR-deficiency[9,15]. Since these markers were not selected based on the relative frequency by which they affect MMR– tumors, this panel sometimes fails to detect MMR– tumors[24]. We therefore assessed whether recurrent mutations could improve detection of MSI.

8.1 Construction of a Diagnostic Panel

There are two criteria by which we believe it is possible to improve the diagnostic panel currently used for detecting microsatellite instability. First of all, we determined recurrent mutations in MMR-deficient tumors in an unbiased way: by performing whole-genome and exome sequencing experiments and simply observing which positions were recurrently affected. Second, the majority of the recurrent indels we identified were located in the 3'UTR, for which no selection could be observed, and for which it is unlikely that tissue-specific enrichments occur. These two criteria ensure that we i) have chosen markers, which without a priori knowledge about their function, are recurrently affected in multiple tumor samples and ii) have a number of markers that are likely to be cancer-type independent.

Since we wanted to optimize the efficiency of our panel, we only used datasets for mutations recurring in 3 or more out of 8 samples. Specifically for the 3'UTR recurrent indels, priority was given to indels affecting 5 or more samples. These 31 recurrent exonic indels, 596 recurrent 3'UTR indels and 30 recurrent 5'UTR indels were consequently used to design an unbiased detection panel for MMR-deficient tumors. Since all recurrent indels were located in homopolymer regions, optimizing primer design and Sequenom MassARRAY design was not without effort. Ultimately, we were able to design assays with high success rate (>90%) for 58 recurrent mutations (12 were located in exonic, 41 in 3'UTR and 5 in 5'UTR, respectively). Full details for these 58 mutations can be found in Table 3 (see description).

This panel was consequently applied to an additional series of 117 unselected endometrial tumors, consisting of 7 clear cell, 70 endometrioid, 18 mixed serous-endometrioid, 12 serous and 10 unclassified endometrial carcinomas, all primary and chemonaïve. The overall success rate of the selected mutations was high (the position could be detected on average in 96.8% of the samples). The number of positive markers for one sample varied between 0 and 34, with an overall average of 6.4 positive markers per sample. The number of samples that were found positive for a specific marker varied between 0 and 32, with an overall average of 12.9. Analogously with the Bethesda panel, we defined three categories of microsatellite instability: microsatellite stable (MSS, 0 out of 5 markers in Bethesda, 0 or 1 out of 58 markers in our panel), low microsatellite instability (MSI-L, 1 out of 5 in Bethesda panel, between 2 and 11 in our panel) and high microsatellite instability (MSI-H, 2 or more out of 5 in Bethesda, 12 or more out of 58 in our panel).

Remarkably, 67 tumors (57.3%) were positive for none or only one of the 58 markers, whereas 29 tumors (24.8%) were positive for at least 12 markers. A considerable proportion of tumors showed an intermediate pattern of MSI (21 or 17.9% of the tumors were positive for >1 but <12 markers; FIG. 11E), suggesting that MSI should be considered as a continuum of low, medium and high instability. Notably, indels in MYL1 and SETD1B were the most frequently detected indels in exons (24 and 20 samples, respectively), whereas indels in the 5' and 3'UTRs occurred most frequently in DIDO1 and UBE2Z (32 samples).

Example 9. MMR Deficiency Causes Similar Mutation Patterns in Various Tumor Types In order to assess whether our observation in MMR− endometrial tumors were extendable to other tumor types, one MMR− ovarian tumor, two MMR+ ovarian tumors and their matched germ-lines as well as three MMR− leukemia cell lines and a MMR+ leukemia cell lines were also analyzed.

9.1 Samples and Clinical Information, Sequencing and Analysis Flow.

In total, 3 ovarian tumor-normal pairs were collected for sequencing, of which only one had the same MSH6 frameshift mutation as the hypermutator whole-genome samples ((MMR− Ovarian 1). All tumors were primary, chemo-naïve tumors. One MMR-deficient ovarian tumor together with its matched germ-line DNA was exome-sequenced using Illumina's TruSeq capture. The same analysis flow for exome data was followed as described earlier. The exome data of two MMR+ ovarian tumors ((MMR+ Ovarian 1 and 2), together with their matched germ-line were extracted from existing whole-genome data. Whole-genome and exome statistics for these three tumor-normal pairs are provided in the tables below.

In addition, 4 commercial cell lines (DND41, CCRF-CEM, SUPT1 and RPMI-8402, T-cell acute lymphoblastic leukemia, DSMZ, http://www.dsmz.de/) were exome-sequenced using Nimblegen capture. DNA was extracted using the Qiagen DNAeasy kit for all samples. Detailed clinical information for all samples is listed in the table below.

| Tumor | Type | Histopathology | Grade | Stage | Mutation status |
|---|---|---|---|---|---|
| MMR− Ovarian | Ovary//Cell culture | Borderline serous carcinoma | 3 | IIIc | |
| MMR+ Ovarian 1 | Ovary | Clear cell carcinoma | 3 | IIc | |
| MMR+ Ovarian 2 | Ovary | Clear cell carcinoma | 3 | IIIc | |
| DND41 | Blood//Cell line | Acute lymphoid leukemia | / | / | |
| CCRF-CEM | Blood//Cell line | Acute lymphoid leukemia | / | / | |
| SUPT1 | Blood//Cell line | Acute lymphoid leukemia | / | / | |
| RPMI8402 | Blood//Cell line | Acute lymphoid leukemia | / | / | |

Overall statistics for the 2 tumor-normal pairs analysed using Complete Genomics' whole-genome sequencing are as follows:

| | MMR+ Ovarian 1 tumor | MMR+ Ovarian 1 matched normal | MMR+ Ovarian 2 tumor | MMR+ Ovarian 2 matched normal |
|---|---|---|---|---|
| Technology used | CG | CG | CG | CG |
| Reference genome | hg18 | hg18 | hg18 | hg18 |
| Bases mapped (Gb) | 171.5 | 247.2 | 190.6 | 171.0 |
| % called bases | 92.1% | 93.1% | 91.4% | 90.9% |
| Haploid coverage | 61.3x | 88.3x | 68.1x | 61.1x |
| Number of substitutions | 3,062,548 | 3,156,112 | 3,037,317 | 3,053,067 |
| Number of indels | 317,302 | 352,356 | 315,285 | 311,269 |

For the MMR-deficient ovarian tumor-normal pair and the 4 leukemia cell lines, the statistics for the exome sequencing experiment are described below.

|  | MMR– Ovarian 1 tumor | MMR– Ovarian 1 matched normal | MMR– Leukemia 1 tumor | MMR– Leukemia 2 tumor | MMR– Leukemia 3 tumor | MMR+ Leukemia 1 tumor |
|---|---|---|---|---|---|---|
| Capture | TruSeq | TruSeq | Nimblegen | Nimblegen | Nimblegen | Nimblegen |
| Number of reads | 4.42E+07 | 8.43E+07 | 2.12E+08 | 1.99E+08 | 2.11E+08 | 2.25E+08 |
| Percent on target | 55.0% | 50.9% | 79.3% | 78.8% | 47.2% | 75.2% |
| Exome covered | 91.9% | 95.3% | 97.3% | 97.2% | 97.4% | 97.2% |
| Mean target coverage | 26.6 | 45.9 | 179.5 | 169.3 | 102.8 | 181.3 |
| Number of substitutions | 50,766 | 52,113 | 32,527 | 34,372 | 40,420 | 31,278 |
| Number of indels | 29,513 | 35,774 | 27,412 | 33,547 | 133,140 | 25,396 |

9.2 Somatic Mutations in a MMR-Deficient Ovarian Tumor

In the MMR-deficient ovarian tumor (MMR– Ovarian 1), 2,045 novel somatic substitutions and 269 novel somatic indels were detected. Because the validation rate in MMR– tumors was very high in general, no further validation was performed for this tumor. In the two MMR+ ovarian tumors, respectively 32 and 42 novel somatic substitutions, and 12 and 18 novel somatic indels were detected. Due to the low validation rate in MMR+ tumors in general, all somatic mutations in the two MMR+ ovarian tumors were validated using Sequenom MassARRAY. Respectively 16 and 20 substitutions were confirmed as true substitutions in the two MMR+ ovarian tumors. No indel was validated in either tumor. The data are summarized in the table below.

| Tumor | Substitutions (validated) | Indels (validated) | Events (validated) |
|---|---|---|---|
| MMR– Ovarian 1 | 2,045 | 269 | 2,314 |
| MMR+ Ovarian 1 | 32 (16) | 12 (0) | 44 (16) |
| MMR+ Ovarian 2 | 42 (20) | 18 (0) | 60 (20) |

9.3 Somatic Mutations in MMR-Deficient Acute Lymphoblastic Leukemia

The exomes of four leukemia cell lines were sequenced using Illumina HiSeq technology. Since there was no matched germ-line DNA available for these cell lines, we could not distinguish between somatic or germ-line mutations. However, using a common variant filtering pipeline we could eliminate frequently occurring variants from the overall list. The table below lists the number of novel substitutions and indels observed in the four leukemia cell lines.

| Cell line ID | Tumor | Substitutions | Indels | Events |
|---|---|---|---|---|
| DND41 | MMR– Leukemia 1 | 5,123 | 692 | 5,812 |
| CCRF-CEM | MMR– Leukemia 2 | 5,789 | 698 | 6,487 |
| SUPT1 | MMR– Leukemia 3 | 6,021 | 976 | 6,997 |
| RPMI8402 | MMR+ Leukemia | 3,602 | 247 | 3,849 |

9.4 Recurrent Mutations in Leukemia and Ovarian Exomes

In order to assess whether recurrent mutations were tumor-type specific, we compared the recurrent mutation lists derived from the endometrial MMR– exome to the mutation data derived from the ovarian and leukemia MMR– exomes. Firstly, of the 130 mutations present in at least 2 out of 8 endometrial tumors, 65, 29, 9 and 1 mutations were also present in at least 1, 2, 3 and 4 out of 4 ovarian and leukemia tumors. Secondly, of the 34 mutations recurring in at least 3 out of 8 endometrial tumors, 28, 12, 6 and 1 were present in at least 1, 2, 3 and 4 out of 4 ovarian and leukemia MMR– tumors.

9.5 Application of the 58-Marker Panel to a Series of MMR-Deficient Colorectal Tumors Six colorectal tumors with proven MMR-deficiency were tested using the 58-marker panel shown in Table 3. The samples were evaluated using diagnostic assays described earlier, for which results are shown in the table below. Overall, between 25 and 36 out of 58 markers were positive for each sample, with a mean of 31.0 markers. Thus, each sample is detected as MSI-H. For the 58 markers, between 0 and 6 out of 6 samples were found positive, with an average of 3.2 positive samples per marker.

| Sample | Mutation status | MSI-score | IHC MLH1 | IHC MSH2 | IHC MSH6 |
|---|---|---|---|---|---|
| Sample 1 | MLH1 exon 12 c.1334delA | 5/8 | N | P | P |
| Sample 2 | MSH2 exon 3 c.440_441delTT | 6/8 | N/A | N/A | N/A |
| Sample 3 | MSH2 exon 3 c.437delG | 5/10 | P | N | N |
| Sample 4 | MSH2 exons 1-7 deleted | 2/6 | N/A | N/A | N/A |
| Sample 5 | MSH6 exon 4 c.1569_1572delTTAC | 5/6 | P | P | N |
| Sample 6 | MSH6 exon 4 c.1444C > T (p.R482X) | 3/10 | P | P | N |

Summary

We assessed whether recurrent mutation patterns in endometrial MMR– tumors were extendable to other tumor types. We sequenced the exomes of an MMR– ovarian tumor with a frameshift deletion in MSH6 (rs63750431) and an MMR+ ovarian tumor together with their matched germ-line DNA. The number of somatic events was drastically increased in the MMR– tumor (2,045 substitutions and 269 indels versus 18 substitutions and 0 indels in the MMR+ exome). We also sequenced an acute lymphoblastic leukemia cell line with a frameshift deletion in MSH6 (DND41, rs63750431), 2 MMR-deficient leukemia cell lines (CCRF-CEM and SUPT1) with mutations in MLH1 (R100X and T495fs) and a MMR+ leukemia cell line (RPMI8402). Since there was no matched germ-line DNA available for these cell lines, we could not distinguish between somatic or germ-line mutations. Nevertheless, an increase in the number of substitutions and indels was seen in the MMR− cell lines (5,644 substitutions and 789 indels versus 3,602 substitutions and 247 indels in the MMR+ cell line). When assessing whether recurrent mutations identified in endometrial tumors were also present in the ovarian and leukemia genomes, we noticed that out of the 384 recurrent mutations in endometrial MMR− tumors, 60, 25, 8 and 1 were present in respectively 1, 2, 3 or 4 MMR− tumors (FIG. 11F). A more pronounced enrichment was seen when limiting the recurrent mutations to those that were present in 3 out 8 endometrial tumors. Of all 32 such recurrent mutations, 27, 12, 6 and 1 were present in 1, 2, 3 or all 4 MMR− tumors (FIG. 11F). Finally, since recurrent indels in the exome are positively selected by the tumor tissue whereas recurrent indels in 5' and 3'UTRs largely depend on the length of the homopolymer, indels in UTRs might represent better markers of MSI. To assess this possibility, we screened 9 colorectal MMR-deficient tumors with proven MSI for our set of 58 recurrent markers. On average, 38.6% of the exonic and 54.7% of the 3' and 5'UTR markers were positive (FIG. 11G).

REFERENCES

1 Stratton, M. R., Campbell, P. J. & Futreal, P. A. The cancer genome. Nature 458, 719-724 (2009).
2 Futreal, P. A. et al. A census of human cancer genes. Nat Rev Cancer 4, 177-183 (2004).
3 Loeb, L. A., Loeb, K. R. & Anderson, J. P. Multiple mutations and cancer. Proc Natl Acad Sci USA 100, 776-781 (2003).
4 Loeb, L. A., Springgate, C. F. & Battula, N. Errors in DNA replication as a basis of malignant changes. Cancer Res 34, 2311-2321 (1974).
5 Loeb, L. A. Human cancers express mutator phenotypes: origin, consequences and targeting. Nat Rev Cancer 11, 450-457 (2011).
6 Poulogiannis, G., Frayling, I. M. & Arends, M. J. DNA mismatch repair deficiency in sporadic colorectal cancer and Lynch syndrome. Histopathology 56, 167-179 (2010).
7 Beckman, R. A. & Loeb, L. A. Negative clonal selection in tumor evolution. Genetics 171, 2123-2131 (2005).
8 Jones, S. et al. Frequent mutations of chromatin remodeling gene ARID1A in ovarian clear cell carcinoma. Science 330, 228-231 (2010).
9 Boland C R, Thibodeau S N, Hamilton S R, et al: A National Cancer Institute Workshop on Microsatellite Instability for cancer detection and familial predisposition: Development of international criteria for the determination of microsatellite instability in colorectal cancer. Cancer Res 58:5248-5257, 1998.
10 Palomaki G E, McClain M R, Melillo S, et al: EGAPP supplementary evidence review: DNA testing strategies aimed at reducing morbidity and mortality from Lynch syndrome. Genetics in Medicine 11:42-65, 2009.
11 Popat S, Hubner R, Houlston R S: Systematic review of microsatellite instability and colorectal cancer prognosis. J Clinl Oncol 23.609-617, 2005.
12 Ribic C M, Sargent D J, Moore M J, et al: Tumor microsatellite-instability status as a predictor of benefit from Fluorouracil-based adjuvant chemotherapy for colon cancer. N Engl J Med 349:247-257, 2003.
13 Des Guetz G, Schischmanoff O, Nocalas P, et al: Does microsatellite instability predict the efficacy of adjuvant chemotherapy in colorectal cancer? A systematic review with meta-analysis. Euro J Cancer 45:1890-1896, 2009.
14 Dietmaier, W. et al. Diagnostic microsatellite instability: definition and correlation with mismatch repair protein expression. Cancer Res 57, 4749-4756 (1997).
15 Umar, A. et al. Revised Bethesda Guidelines for hereditary nonpolyposis colorectal cancer (Lynch syndrome) and microsatellite instability. J Natl Cancer Inst 96, 261-268 (2004).
16 de la Chapelle, A. & Hampel, H. Clinical relevance of microsatellite instability in colorectal cancer. J Clin Oncol 28, 3380-3387 (2010).
17 Pyatt R, Chadwick R B, Johnson C K, et al: Polymorphic variation at the BAT-25 and BAT-26 loci in individuals of African origin: Implications for microsatellite instability testing. Am J Pathol 155:349-353, 1999.
18 Lindor, N. M. et al. Immunohistochemistry versus microsatellite instability testing in phenotyping colorectal tumors. J Clin Oncol 20, 1043-1048 (2002).
19 Simpkins, S. B. et al. MLH1 promoter methylation and gene silencing is the primary cause of microsatellite instability in sporadic endometrial cancers. Hum Mol Genet. 8, 661-666 (1999).
20 Herman, J. G. et al. Incidence and functional consequences of hMLH1 promoter hypermethylation in colorectal carcinoma. Proc Natl Acad Sci USA 95, 6870-6875 (1998).
21 Quinlan, A. R. & Hall, I. M. BEDTools: a flexible suite of utilities for comparing genomic features. Bioinformatics 26, 841-842 (2010).
22 Banerjea, A. et al. Colorectal cancers with microsatellite instability display mRNA expression signatures characteristic of increased immunogenicity. Mol Cancer 3, 21 (2004).
23 Kapushesky, M. et al. Gene expression atlas at the European bioinformatics institute. Nucleic Acids Res 38, D690-698 (2010).
24 Pinol, V. et al. Accuracy of revised Bethesda guidelines, microsatellite instability, and immunohistochemistry for the identification of patients with hereditary nonpolyposis colorectal cancer. JAMA 293, 1986-1994 (2005).
25 Hewish, M., Lord, C. J., Martin, S. A., Cunningham, D. & Ashworth, A. Mismatch repair deficient colorectal cancer in the era of personalized treatment. Nat Rev Clin Oncol 7, 197-208 (2010).
26 Heijink, D. M. et al. Perspectives for tailored chemoprevention and treatment of colorectal cancer in Lynch syndrome. Crit Rev Oncol Hematol (2010).

The invention claimed is:
1. A kit for determining microsatellite instability in 4 to 107 microsatellite regions of a tumor or cancer sample, the kit comprising:
    labeled oligonucleotides to specifically genotype 4 to 107 microsatellite regions selected from those present in 5' UTR or 3' UTR regions from the genes listed in Table 1,
    wherein each of the labeled oligonucleotides comprises a sequence specifically hybridizing to one of the microsatellite regions;

wherein the maximal amount of the labelled oligonucleotides the kit comprises is limited to the number necessary to specifically genotype the 4 to 107 microsatellite regions; and wherein the label of the labeled oligonucleotides is a non-nucleic acid label.

2. The kit of claim 1, wherein the labeled oligonucleotides are labeled primers.

3. The kit of claim 1, wherein the labeled oligonucleotides are labeled probes.

4. A kit for determining microsatellite instability in 4 to 138 microsatellite regions of a tumor or cancer sample, the kit comprising:

labeled oligonucleotides to specifically genotype 4 to 138 microsatellite regions selected from those present in 5' UTR or 3' UTR regions from the genes listed in Table 1 and those present in the exons of the genes listed in Table 2, wherein the labeled oligonucleotides are 4 to 138 microsatellite region-specific primer and probe sets;

wherein at least one primer or probe of each set comprises a sequence specifically hybridizing to one of the microsatellite regions;

wherein at least one of the primer or probe of each set is labeled;

wherein the label of the labeled oligonucleotides is a non-nucleic acid label.

5. The kit of claim 4 further comprising labeled oligonucleotides to genotype the microsatellite instability markers of a Bethesda panel or extended Bethesda panel.

6. A kit for determining microsatellite instability in 4 to 50 microsatellite regions of a tumor or cancer sample, the kit comprising labeled oligonucleotides to specifically genotype 4 to 50 of the microsatellite regions selected from the group consisting of those present in 5' UTR or 3' UTR regions from the genes listed in Table 1 and those present in the exons of the genes listed in Table 2;

wherein the maximal amount of the labeled oligonucleotides the kit comprises for determining microsatellite instability is limited to the number necessary to specifically genotype the 4 to 50 microsatellite regions; and wherein the label of the labeled oligonucleotides is a non-nucleic acid label.

7. The kit of claim 6 further comprising labeled oligonucleotides to genotype the microsatellite instability markers of a Bethesda panel or extended Bethesda panel.

8. A kit for determining microsatellite instability in 4 to 50 microsatellite regions of a tumor or cancer sample, the kit comprising sets of oligonucleotides to specifically genotype 4 to 50 of the microsatellite regions selected from the group consisting of those present in 5' UTR or 3' UTR regions from the genes listed in Table 1 and those present in the exons of the genes listed in Table 2, wherein each set comprises a primer and probe(s) of which at least one is labeled;

wherein the maximal amount of sets of oligonucleotides the kit comprises for determining microsatellite instability is limited to the number necessary to specifically genotype the 4 to 50 microsatellite regions; and wherein the label of the labeled primer or probe is a non-nucleic acid label.

9. A kit for determining microsatellite instability in at least 4 microsatellite regions of a tumor or cancer sample, the kit comprising:

labeled oligonucleotides to genotype at least 4 of the microsatellite regions selected from the group consisting of those present in 5' UTR or 3' UTR regions from the genes listed in Table 1 and those present in the exons of the genes listed in Table 2, wherein each of the labeled oligonucleotides comprises a sequence specifically hybridizing to one of the microsatellite regions;

wherein the maximal amount of the labeled oligonucleotides the kit comprises is limited to the number necessary to specifically genotype the at least 4 microsatellite regions; and wherein the label of the labeled oligonucleotides is a non-nucleic acid label.

10. A kit for determining microsatellite instability in 4 to 138 microsatellite regions of a tumor or cancer sample, the kit comprising:

labeled oligonucleotides to genotype 4 to 138 microsatellite regions selected from those present in 5' UTR or 3' UTR regions from the genes listed in Table 1 and those present in the exons of the genes listed in Table 2, wherein each of the labeled oligonucleotides comprises a sequence specifically hybridizing to one of the microsatellite regions;

wherein the maximal amount of the labeled oligonucleotides the kit comprises is limited to the number necessary to specifically genotype the 4 to 138 microsatellite regions; and wherein the label of the labeled oligonucleotides is a non-nucleic acid label.

11. A method of diagnosing microsatellite instability ("MSI") status of a tumor, the method comprising:

determining the presence of an indel in at least two microsatellite regions in a sample of the tumor's DNA utilizing the kit of claim 10, wherein the presence of at least one indel is indicative of MSI.

12. The method according to claim 11, wherein the microsatellite regions are homopolymer regions.

13. The method according to claim 11, wherein the microsatellite regions are identical to the microsatellite regions identified in Table 1 or 2.

14. The method according to claim 11, wherein the tumor is selected from the group consisting of colorectal cancer, endometrial cancer, ovarian cancer, gastric cancer, leukemia, and a tumor of Lynch syndrome.

15. The method according to claim 11, wherein the microsatellite regions of the kit comprise at least two microsatellite regions selected from those present in 5' UTR or 3' UTR regions from the genes listed in Table 1 and at least two microsatellite regions selected from those present in the 20 exons of the genes listed in Table 2.

16. The method according to claim 11, wherein the microsatellite regions of the kit comprise at least one microsatellite selected from the following genes: SETD1B, RBMXL1, CCDC150, TMEM60, DDX27, EXOSC9, FAM111B, KIAA0182, KIAA1919, OR7E24, P4HTM, PRRT2, RNPC3, and TMEM97.

17. The method according to claim 11, wherein the kit comprises 40 microsatellite regions selected from Table 3.

18. The method according to claim 11, wherein the MSI is characterized as follows:

if 20% or more of the microsatellite regions contains an indel, the tumor is MSI-H, if between 2% and 20% of the microsatellite regions contains an indel, the tumor is MSI-L, and if less than 2% of the microsatellite regions contains an indel, the tumor is microsatellite stable.

19. The method according to claim 11, wherein determining the presence of an indel is not done through a method based on Sanger sequencing.

20. The method according to claim 11, wherein determining the presence of an indel is done through single base pair extension technologies or DNA hybridization technologies.

21. A method of determining microsatellite instability ("MSI") status in a tumor, the method comprising:

determining the presence of an indel in at least two microsatellite regions in a sample of the tumor's DNA utilizing the kit of claim 10, wherein at least two of the microsatellite regions are at least two microsatellite regions present in 5' UTR or 3' UTR regions from the genes listed in Table 1, or at least three microsatellite regions selected from those present in the exons of the genes listed in Table 2 and/or present in 5' UTR or 3' UTR regions from the genes listed in Table 1, wherein the microsatellite regions are homopolymer regions and are identical to the microsatellite regions identified in Table 1 or 2, wherein determining the presence of an indel is done through single base pair extension technologies or DNA hybridization technologies, and wherein the MSI is characterized as follows:

if 20% or more of the microsatellite regions contains an indel, the tumor is MSI-H, if between 2% and 20% of the microsatellite regions contains an indel, the tumor is MSI-L, and if less than 2% of the microsatellite regions contains an indel, the tumor is microsatellite stable.

22. The method according to claim 21, wherein the at least two of the microsatellite regions are at least two microsatellite regions selected from those present in 5' UTR or 3' UTR regions from the genes listed in Table 1 and at least two microsatellite regions selected from those present in the twenty exons of the genes listed in Table 2.

23. The method according to claim 22, wherein the microsatellite(s) selected from those present in the exons of the genes listed in Table 2 comprises at least one microsatellite selected from the group consisting of SETD1B, RBMXL1, CCDC150, TMEM60, DDX27, EXOSC9, FAM111B, KIAA0182, KIAA1919, OR7E24, P4HTM, PRRT2, RNPC3, and TMEM97.

24. The method according to claim 21, wherein the microsatellite regions of the kit comprise forty microsatellite regions selected from Table 3.

* * * * *